(12) United States Patent
Liu

(10) Patent No.: US 8,507,646 B2
(45) Date of Patent: Aug. 13, 2013

(54) TREATING ATHEROSCLEROSIS

(75) Inventor: Jian-Ning Liu, Auburndale, MA (US)

(73) Assignee: Landing Biotech, Inc., Auburndale, MA (US)

( * ) Notice: Subject to any disclaimer, the term of this patent is extended or adjusted under 35 U.S.C. 154(b) by 745 days.

(21) Appl. No.: 12/528,300

(22) PCT Filed: Feb. 23, 2007

(86) PCT No.: PCT/US2007/004899
§ 371 (c)(1),
(2), (4) Date: Feb. 1, 2010

(87) PCT Pub. No.: WO2008/103146
PCT Pub. Date: Aug. 28, 2008

(65) Prior Publication Data
US 2010/0143335 A1    Jun. 10, 2010

(51) Int. Cl.
*A61K 38/00* (2006.01)
*C07K 14/00* (2006.01)

(52) U.S. Cl.
USPC ........................ 530/300; 424/130.1

(58) Field of Classification Search
None
See application file for complete search history.

(56) References Cited

U.S. PATENT DOCUMENTS

| 5,236,705 | A | * | 8/1993 | Hamilton et al. | 424/85.2 |
| 5,472,692 | A | * | 12/1995 | Liu et al. | 424/94.63 |
| 6,248,712 | B1 | | 6/2001 | Danoe et al. | |
| 6,811,782 | B1 | | 11/2004 | Wang et al. | |
| 2002/0131964 | A1 | | 9/2002 | Cines et al. | |
| 2007/0225323 | A1 | | 9/2007 | Lang et al. | |

FOREIGN PATENT DOCUMENTS

| EP | 0139447 | * | 9/1984 |
| EP | 0 319 447 | | 6/1989 |

OTHER PUBLICATIONS

Office Action in EP Application No. 07 751 643.3-2404; mailed Mar. 8, 2011 (6 pages).
European Search Report, 07751643.3; mailed Apr. 19, 2010.
Falkenberg et al., "Increased Expression of Urokinase During Atherosclerotic Lesion Development Causes Arterial Constriction and Lumen Loss, and Accelerates Lesion Growth," Proceedings of the National Academy of Sciences of the United States of America, vol. 99, No. 16, Aug. 6, 2002, pp. 10665-10670.
Huai Qing et al., "Structure of Human Urokinase Plasminogen Activator in Complex with its Receptor," Science, vol. 311, No. 5761, Feb. 3, 2006, pp. 656-659.
Cozen et al., "Mactrophage-Targeted Overexpression of Urokinase Causes Accelerated Atherosclerosis, Coronary Artery Occlusions, and Premature Death," *Circulation* 109:2129-2135, 2004.
European Patent Office—Summons to Attend Oral Proceedings, Application No. 07751643.2-2404; Feb. 14, 2012 (6 pages).
International Search Report and Written Opinion; Application No. PCT/US07/04899; mailed Sep. 10, 2008, 11 pages.
Office Action; European Application No. 07751643.3-2404; mailed Mar. 8, 2011; 6 pages.
European Patent Office—Summons to Attend Oral Proceedings, Application No. 07751643.2-2404; Nov. 2, 2012; 6 pages.

* cited by examiner

*Primary Examiner* — Anand Desai
(74) *Attorney, Agent, or Firm* — Fish & Richardson P.C.

(57) ABSTRACT

The present application features methods and compositions for treating patients suffering from atherosclerosis or at risk for developing atherosclerosis. The treatment includes administering to the patient a pharmaceutical composition that includes an agent capable of blocking the interaction between uPA and its receptor uPAR, e.g., an ATF or a fragment thereof, an anti-uPA antibody, a uPAR or a fragment thereof, or an antibody that specifically binds to uPAR.

11 Claims, 19 Drawing Sheets

Multiple sequence alignment of ATF

```
                        0         10        19        31    41  45 48
Human   (SEQ ID NO:1)   ----------SNELHQVP--SNCDCLNGGTCVSNKYFSNIHWCNCPKKFGGQHCEIDKSKTCY    51
Baboon  (SEQ ID NO:2)   ----------SREL-QVF--SDCGCLNGGRCMSNRYFSSIHWCNCPKKFQGQHCEIDKSKTCY    50
Mouse   (SEQ ID NO:3)   ---------GSVLGAFDESNCGCQNGGVCVSYKYFSSRIRRCSCPRKFQGEHCEIDASKTCY    52
Rat     (SEQ ID NO:4)   ---------GSELEASDESNCGCQNGGVCVSYKYFSSTRRCSCPKKEGEHCEIDTSKTCY    52
Cow     (SEQ ID NO:5)   ----------SNEVHKESGSNCGCLNGGKCVTIKYFSNIHRCSCPKKFQGEHCEIDTSKTCY    53
Pig     (SEQ ID NO:6)   ----------SHELHQESGASNCGCLNGGKCVSYKYFSNIQRCSCPKKEQGEHCEIDTSQTCF    53
Chicken (SEQ ID NO:7)   VTIRQYYKLSHKHRPQHREQCCLNGSTCITIYRFFSQLRKCLCPECYGGLHCEIDTNSICY    60

52  56    63 67  73 76 81 83        89     94
Human      EGNGHFYRGKASTDTMGRPCLPWNSATVLQQ--TYHAHRSDALQLGLGKHNYCRNPDNRRR     110
Baboon     GNGHFYRGKASTDTMGRSCLAWNSATVLQQ--TYHAHRSDALQLGLGKHNYCRNPDNRRR     109
Mouse      HGNGDSYRGKANTDTKGRPCLAWNACADG--PYNAHRPDAISLGLGKHNYCRNPDNQKR     111
Rat        HGNGQSYRGKANTDTKGRPCLAWNSPAVLQQ--TYNAHRSDALSLGLGKHNYCRNPDNQKR     111
Cow        QGNGHSYRGKANRDLSGKFCLAWDSPTVLLK--MYHAHRSDAIQLGLGKHNYCRNPDNQRR     112
Pig        EGNGHSYRGKANTWTGGRPCLPWNSATVLLN--TYHAHRPDALQLGLGKHNYCRNPDNQRR     112
Chicken    SGNGEDYRGMAEDPG----CLYWDHPSVIRWGDYHADLKNALQLGLGKHNYCRNPNGRSR     116

114 121    129 133       136       143 146
Human      PWCYVQVGLKPLVQECMVHDCADG-------KKPSSSPFEELKFQCCQKTLRPRF     157
Baboon     PWCYVQVGLKQRVQECMVHDCMVHNCADG--------KKPSSSPFEELQPQCGQRTLRPRF     156
Mouse      PWCYVQIGLRQFVQECMVHDCSLS-------------KKPSSSVDQGGFQCGQKALRPRF     158
Rat        PWCYVQIGLKQFVQECMVQDCSLS-------------KKPSSTVDQGGFQCGQKALRPRF     158
Cow        PWCYVQIGLKQFVQFCMVQDCSVG-------------KSPSSPREKEEFQCCGQKALRPRF     159
Pig        PWCYVQVGLKQLVQECMVPNCSGGESHRFAYDGKNFESTPKVEFQCGQKALRPRF        168
Chicken    PWCYTKR----RVSIQET-------------------PCSTIEKCERTCGQRSFSKYF   151
```

FIG. 1

Receptor binding loops of human, rabbit, and mouse ATFs

```
            The receptor-binding loop
            |--------------------|
CLNGGTCVTYKYFSNIWRCNCPKKFQGEHCEIDTLKTCYHGDGHSYRGKANTDIMDRPCLAWNSANVL   --rabbit
CLNGGTCVSNKYFSNIH Amino acid sequence and secondary structure of human uPAR >gi|8050815|gb|AAF71751.1| urokinase-type plasminogen activator receptor; UPAR [Homo sapiens]

MGHPPLLPLLLLLHTCVPASWGLRCMQCKTNGDCRVEECALGQDLCRTTIVRLWEEGEELELVEKSCTHS
EKTNRTLSYRTGLKITSLTEVVCGLDLCNQGNSGRAVTYSRSRYLECISCGSSDMSCERGRHQSLQCRSP
EEQCLDVVTHWIQEGEEGRPKDDRHLRGCGYLPGCPGSNGFHNNDTFHFLKCCNTTKCNEGPILELENLP
QNGRQCYSCKGNSTHGCSSEETFLIDCRGPMNQCLVATGTHGPKNQSYMVRGCATASMCQHAHLGDAFSM
NHIDVSCCTKSGCNHPDLDVQYRSGAAPQPGPAHLSLTITLL (SEQ ID NO:8)

FIG. 3

| Lesion area percentage (%) | 1 | 2 | 3 | 4 | ave | P |
|---|---|---|---|---|---|---|
| Control | 55.95 | 62.51 | 51.92 | 46.01 | 54.0975 | 0.12 |
| Ab s.c. | 37.98 | 48.75 | 49.22 | 48.38 | 46.0825 | |

| Lesion area percentage (%) | 1 | 2 | 3 | 4 | ave | P |
|---|---|---|---|---|---|---|
| Control | 41.17 | 47.78 | 51.92 | 46.01 | 46.72 | $1.32*10^{-5}$ |
| Vaccination/rhATF | 7.88 | 2.52 | 6.99 | 12.60 | 7.50 | |

TREATING ATHEROSCLEROSIS

CROSS-REFERENCE TO RELATED APPLICATIONS

This application is the U.S. national stage under 35 USC §371 of International Application Number PCT/US2007/004899, filed on Feb. 23, 2007, the entire contents of which are hereby incorporated by reference.

TECHNICAL FIELD

This invention relates to methods of treating atherosclerosis.

BACKGROUND

Atherosclerosis is an inflammatory disease in which fatty material collects along the walls of arteries. Lusis, *Nature*, 407:233-241 (2000).

Urokinase-type plasminogen activator (uPA) promotes inflammatory cell adhesion and migration through binding to urokinase plasminogen activator receptor (uPAR). Gu et al., *J. Cell Physiol.*, 204(1):73-82. uPA over-expressed by macrophages accumulates at atherosclerotic lesions, resulting in accelerated atherosclerosis. Cozen et al., *Circulation*, 109 (17):2129-35 (2004). uPA receptor (uPAR) promotes macrophage infiltration into vascular walls in ApoE deficient mice, which is a mouse model for atherosclerosis. Gu et al., *J. Cell Physiol.*, 204(1):73-82 (2005). Although all these results indicate that uPA/uPAR might play a role in the development of atherosclerosis, genetic depletion of uPA did not affect the formation of atherosclerotic lesions in ApoE deficient mice. Carmeliet et al., *Nat. Genet.*, 17(4):439-44 (1997); Deng et al., *Circ Res.*, 92(5):510-517 (2003).

The amino terminal fragment (ATF) of uPA is responsible for binding to uPAR. Both ATF and anti-ATF antibodies have been reported to be effective in treating cancer. Li et al., *Hum. Gene Ther.*, 16(10):1157-67; Mazar et al., U.S. Patent Application 2005/0232924.

SUMMARY

The present invention is based, in part, on the discovery that certain agents, e.g., an ATF polypeptide, an anti-ATF antibody, a uPAR polypeptide, or an anti-uPAR antibody, are useful for treating atherosclerosis and inhibiting the onset of atherosclerosis.

Accordingly, in one aspect, the application describes methods of treating a patient either suffering from or at risk for atherosclerosis by administering to the patient a composition that includes an ATF polypeptide, i.e., a polypeptide that includes an ATF amino acid sequence, e.g., an ATF protein, polypeptide, or peptide.

The ATF polypeptides can be coupled with one or more agents that extend the half-life of the polypeptide in the patient. For example, the polypeptides can be conjugated with polyethylene glycol (PEG). Alternatively or in addition, the polypeptides can be fused to albumin or other agents known to extend the half-life of polypeptides in vivo.

The ATF polypeptides can be naturally occurring or synthetic. For example, the ATF polypeptides can be a full-length ATF derived from a mammalian species (e.g., human, baboon, mouse, rat, cow, or pig) or a non-mammalian species (e.g., chicken). The ATF polypeptides can be a variant of human ATF protein, for example, a polypeptide having an amino acid sequence at least 70%, 80%, 90%, 95%, or 99% identical to human ATF (SEQ ID NO:1). They can be a chimeric human ATF, e.g., one produced by replacing the receptor binding loop of human ATF with a receptor binding loop derived from an ATF of a non-human species (e.g., baboon, mouse, rat, cow, pig, or chicken).

The ATF polypeptides can be formulated as pharmaceutical compositions, which can include a pharmaceutically acceptable carrier and/or an adjuvant. The compositions can be administered, e.g., intravenously, in one or more doses to the patient. They can be administered before, during, and/or after development of atherosclerosis in the patient.

In another aspect, the application describes pharmaceutical compositions that include the chimeric human ATF molecules described herein. The compositions can include an adjuvant.

In yet another aspect, the application provides isolated polypeptides that include an ATF fragment capable of either binding to a uPAR or inducing an anti-ATF immune response in a patient. Exemplary amino acid sequences of exemplary fragments include:

| (1)  | YRGKASTDT  | (SEQ ID NO: 19) |
|------|------------|-----------------|
| (2)  | WCYVQVGLK  | (SEQ ID NO: 20) |
| (3)  | VGLKPLVQE  | (SEQ ID NO: 21) |
| (4)  | YVQVGLKPL  | (SEQ ID NO: 22) |
| (5)  | MVHDCADGK  | (SEQ ID NO: 23) |
| (6)  | WNSATVLQQ  | (SEQ ID NO: 24) |
| (7)  | YVQVGLKQR  | (SEQ ID NO: 25) |
| (8)  | VGLKQRVQE  | (SEQ ID NO: 26) |
| (9)  | YRGKANTDT  | (SEQ ID NO: 27) |
| (10) | FQCGQKALR  | (SEQ ID NO: 28) |
| (11) | FSRIRRCSC  | (SEQ ID NO: 29) |
| (12) | WCYVQIGLRI | (SEQ ID NO: 30) |
| (13) | IRRCSCPRK  | (SEQ ID NO: 31) |
| (14) | YVQIGLRQF  | (SEQ ID NO: 32) |
| (15) | VQIGLRQFV  | (SEQ ID NO: 33) |
| (16) | YKYFSRIRR  | (SEQ ID NO: 34) |
| (17) | MVHDCSLSK  | (SEQ ID NO: 35) |
| (18) | YFSRIRRCS  | (SEQ ID NO: 36) |
| (19) | FSSIRRCSC  | (SEQ ID NO: 37) |
| (20) | WCYVQIGLK  | (SEQ ID NO: 38) |
| (21) | IRRCSCPKK  | (SEQ ID NO: 39) |
| (22) | WNSPAVLQQ  | (SEQ ID NO: 40) |
| (23) | YFSSIRRCS  | (SEQ ID NO: 41) |
| (24) | YVQIGLKQF  | (SEQ ID NO: 42) |
| (25) | YKYFSSIRR  | (SEQ ID NO: 43) |
| (26) | MVQDCSLSK  | (SEQ ID NO: 44) |
| (27) | FSNIQRCSC  | (SEQ ID NO: 45) |

| | | |
|---|---|---|
| (28) | YFSNIQRCS | (SEQ ID NO: 46) |
| (29) | YKYFSNIQR | (SEQ ID NO: 47) |
| (30) | YRGKANRDL | (SEQ ID NO: 48) |
| (31) | VQFCMVQDC | (SEQ ID NO: 49) |
| (32) | VQIGLKQFV | (SEQ ID NO: 50) |
| (33) | MVQDCSVGK | (SEQ ID NO: 51) |
| (34) | LKMYHAHRS | (SEQ ID NO: 52) |
| (35) | FSNIQRCSC | (SEQ ID NO: 53) |
| (36) | YRGKANTNT | (SEQ ID NO: 54) |
| (37) | WCYVQVGLK | (SEQ ID NO: 55) |
| (38) | WNSATVLLN | (SEQ ID NO: 56) |
| (39) | VGLKQLVQE | (SEQ ID NO: 57) |
| (40) | YFSNIQRCS | (SEQ ID NO: 58) |
| (41) | YVQVGLKQL | (SEQ ID NO: 59) |
| (42) | YKYFSNIQR | (SEQ ID NO: 60) |
| (43) | VYIRQYYKL | (SEQ ID NO: 61) |
| (44) | VIRWGDYHA | (SEQ ID NO: 62) |
| (45) | YYKLSHKHR | (SEQ ID NO: 63) |
| (46) | YHADLKNAL | (SEQ ID NO: 64) |
| (47) | WCYTKRRYS | (SEQ ID NO: 65) |
| (48) | FFSQIKRCL | (SEQ ID NO: 66) |
| (49) | LYWDHPSVL | (SEQ ID NO: 67) |
| (50) | YRFFSQIKR | (SEQ ID NO: 68) |
| (51) | YSIQETPCS | (SEQ ID NO: 69) |
| (52) | IRQYYKLSH | (SEQ ID NO: 70) |
| (53) | YKYFSNIWR | (SEQ ID NO: 71) |

Further, the application describes pharmaceutical compositions that include the polypeptides described herein. These compositions can induce an immune response when administered to a patient. The application also describes antibodies that specifically bind to these polypeptides.

In still another aspect, the application features isolated polypeptides that include, e.g., consist of, a fragment of SEQ ID NO:8. This fragment includes at least one human ATF binding site, e.g., T8, R25, V29, L31, L40, R53, L55, Y57, L66, E68, R137, K139, R142, H143, R145, H166, H251, L252, D254, or A255. In one example, this fragment contains at least 8 amino acids. In another example, the fragment contains at least 15 amino acids. In yet another aspect, the application provides antibodies that specifically bind to such polypeptides and the use of these antibodies for treating atherosclerosis.

Further, the application provides methods of treating atherosclerosis with antibodies that can bind to human uPAR and block the interaction between human ATF and uPAR.

The application also provides methods of screening compounds capable of blocking the interaction between uPA and uPAR and treating atherosclerosis. Methods of screening for such compounds capable of blocking an interaction, e.g., binding, between two polypeptides are known in the art. An exemplary method includes (a) providing a first polypeptide including an ATF polypeptide or polypeptide fragment (e.g., the receptor binding loop) capable of binding to uPAR, and a second polypeptide including a uPAR fragment (e.g., a fragment including one or more ATF binding sites) capable of binding to uPA under conditions in which the first polypeptide interacts with the second polypeptide; (b) contacting a candidate compound with the first and second polypeptides; and (c) determining whether the candidate compound decreases the level of binding between the first polypeptide and the second polypeptide, wherein a decrease in binding indicates that the candidate compound is a candidate agent for blocking the interaction between uPA and uPAR and treating atherosclerosis. The method can optionally include a step of determining whether the candidate compound exhibits anti-atherosclorotic activity in vitro an/or is capable of treating atherosclerosis in vivo.

Also within the scope of the application is the use of agents that block uPA-uPAR binding (e.g., an ATF polypeptide, an anti-ATF antibody, a uPAR protein, or an anti-uPAR antibody) in the manufacture of medicaments for treating atherosclerosis.

The present application also provides methods of purifying and/or identifying uPA proteins or uPAR proteins with anti-ATF antibodies or anti-uPAR antibodies as described herein under conditions that allow binding between the antibody and uPA or uPAR and isolating the proteins from and/or determining whether the protein is present in the sample.

The term "ATF" refers to the N-terminal domain of a uPA polypeptide or protein that binds to its receptor (uPAR) of the same species. Unlike the C-terminal domain of a uPA, which possesses serine protease activity, ATF has no known catalytic activity. The terms "an ATF protein" and "an ATF polypeptide" are used interchangeably herein (unless otherwise noted) and refer to both a full-length ATF or a fragment thereof, provided that the ATF fragment is capable of either binding to uPAR or inducing an anti-ATF immune response in a patient. An ATF polypeptide can be naturally occurring (e.g., derived from any species that has a urokinase), synthetic, or partially natural and partially synthetic. An ATF polypeptide can be chimeric, i.e., including ATF fragments derived from different species.

The terms "a uPAR protein" and "a uPAR polypeptide" are used interchangeably herein (unless otherwise noted) and refer to a full-length uPAR protein or a fragment thereof, provided that the uPAR fragment is capable of either binding to uPA or inducing an anti-uPAR immune response. The uPAR fragment can include as least 8 amino acid residues, or at least 15 amino acid residues. Alternatively or in addition, it can include one or more uPA binding sites.

The terms "effective amount" and "effective to treat" as used herein, refer to an amount or concentration of an agent utilized for a period of time (including acute or chronic administration and periodic or continuous administration) that is effective within the context of its administration for causing an intended effect or physiological outcome. Effective amounts of an ATF and an anti-uPAR antibody for use in the present invention include, for example, amounts that are effective for preventing or inhibiting atheromatous plaque formation in a patient who is at risk for atherosclerosis, or for ameliorating or reducing the symptoms of atherosclerosis in a patient who is in development or has developed atherosclerosis, or for relieving atherosclerotic symptoms of a patient.

The term "patient" is used throughout the specification to describe an animal, human or non-human, to whom treatment according to the methods of the present invention is provided. Veterinary applications are clearly anticipated by the present invention. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats.

The term "atherosclerosis" used throughout this specification is equivalent to "arteriosclerosis" and "arteriolosclerosis." It is referred to as a hardening or thickening of the arteries resulting from the formation of multiple atheromatous plaques within the arteries, i.e., a deposition of fatty materials inside and along the walls of arteries. See, for example, an NIH site in the Internet, e.g., at World Wide Web address nlm.nih.gov/medlineplus/ency/article/000171.htm. A patient having atherosclerosis refers to a patient who has at least one atheromatous plaque, which can be detected by routine medical procedures. Such a patient can exhibit insufficient blood supply to an organ due to plaque ruptures and/or artery stenosis. He and she can have symptoms such as chest pain if an artery to the heart is involved and/or leg pain when a leg artery is involved. A patient who is "at risk for atherosclerosis" bears one or more risk factors for atherosclerosis, for example, personal or family history of heart diseases, high-fat diet, smoking, obesity, high blood pressure, and/or high blood cholesterol.

The term "treating atherosclerosis" used herein, unless otherwise indicated, means relieving the symptoms of atherosclerosis, reversing, ameliorating, or inhibiting the progress of atherosclerosis, or preventing or inhibiting the formation of atheromatous plaque.

By "polypeptide" is meant any chain of amino acids, regardless of length or post-translational modification (e.g., glycosylation or phosphorylation) and thus covers proteins and peptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict; the present specification, including definitions, will control. The materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a representation of the amino acid sequences of human, baboon, mouse, rat, cow, pig, and chicken ATFs. It also shows their sequence alignment.

FIG. 2 is a representation of the receptor binding loops in rabbit (SEQ ID NO:9), human (SEQ ID NO:10), and mouse (SEQ ID NO:11) ATF.

FIG. 3 is a representation of the amino acid sequence of human uPAR.

FIGS. 9A-1 and 9A-2 are graphs that show the time course of atherosclerotic lesion formation in ApoE−/− mice (for female (FIG. 9A-1) and male (FIG. 9A-2) mice).

Like reference symbols in the various drawings indicate like elements.

DETAILED DESCRIPTION

The present invention is based, at least in part, on the discovery that certain agents, e.g., ATF proteins, can be used to treat atherosclerosis in a patient.

1. Treating Atherosclerosis with an ATF Polypeptide

The treatments described herein include administering to a patient an ATF polypeptide.

a. ATF Polypeptides

Figures 1, 9A:
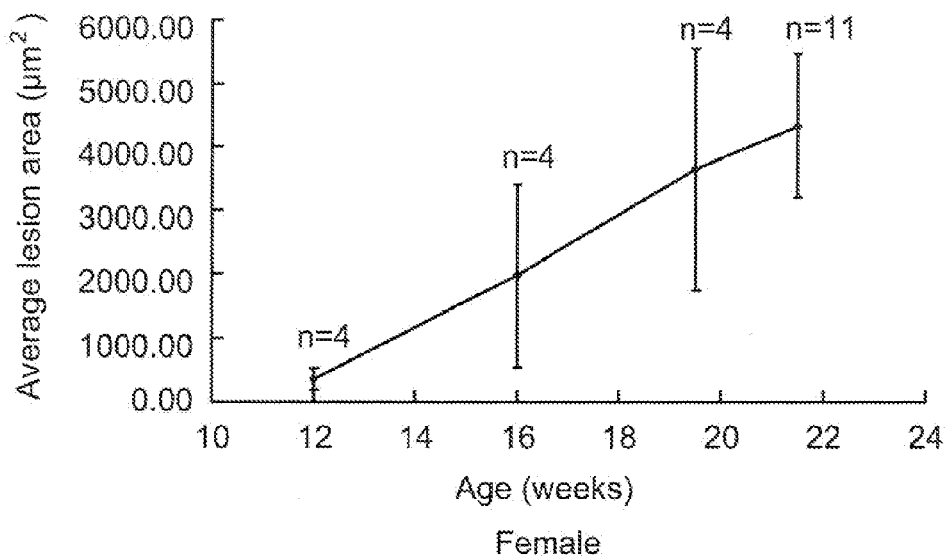

An exemplary ATF polypeptide is human ATF, which includes amino acid residues $Ser_1$-$Lys_{135}$ of human urokinase. The amino acid sequence (SEQ ID NO:1) of human ATF is shown in FIG. 1.

Another exemplary ATF polypeptide is a variant of human ATF, provided that the variant is functionally equivalent to human ATF, i.e., it is capable of binding to at least one type of uPAR. Such variants can possesses anti-atherosclerosis activity, e.g., as determined in an in vivo assay in a test animal. The amino acid sequence of the ATF variants is at least 40%, e.g., 70%, 80%, 90%, 95% or 99%, identical to that of human ATF (SEQ ID NO:1) along its full length. The ATF variant can be an ATF from another species. It can be made, e.g., by inserting mutations into human ATF, e.g., conservative amino acid residue substitutions.

As used herein, "percent identity" of two amino acid sequences is determined using the algorithm of Karlin and Altschul, Proc. Natl. Acad. Sci. USA 87:2264-2268 (1990), modified as in Karlin and Altschul, Proc. Natl. Acad. Sci. USA 90:5873-5877 (1993). Such an algorithm is incorporated into the NBLAST and XBLAST programs of Altschul et al. J. Mol. Biol., 215:403-410 (1990). BLAST protein searches are performed with the XBLAST program, score=50, wordlength=3, to obtain amino acid sequences homologous to a reference polypeptide (e.g., SEQ ID NO:1). To obtain gapped alignments for comparison purposes, Gapped BLAST is utilized as described in Altschul et al., Nucleic Acids Res., 25:3389-3402 (1997). When utilizing BLAST and GAPPED BLAST programs, the default parameters of the respective programs (e.g., XBLAST and NBLAST) are used.

Still another exemplary ATF is one derived from a non-human species, such as bird (e.g., chicken), reptile, or mammal (e.g., monkey, baboon, mouse, rat, rabbit, cow, or pig). As shown in FIG. 1, the ATF domain of urokinase is well characterized in many species, e.g., human, baboon, mouse, rat, cow, pig, and chicken. Given the structural similarity of ATF across species, skilled practitioners can easily determine ATF domains by comparing the amino acid sequence of a urokinase having an unknown ATF domain with the amino acid sequence of the urokinase polypeptides described herein having a known ATF domain.

Figures 2, 9A:
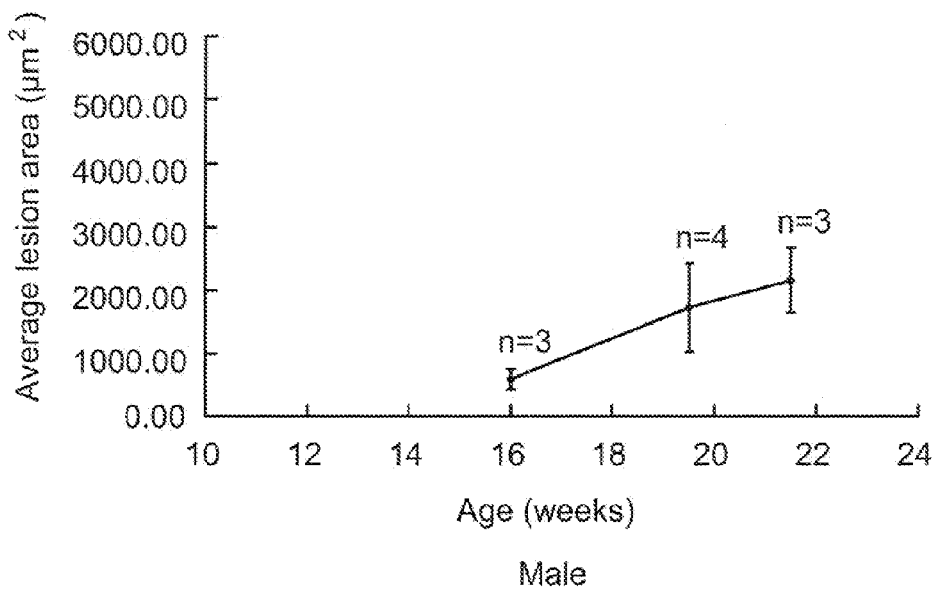
Figure 9B:
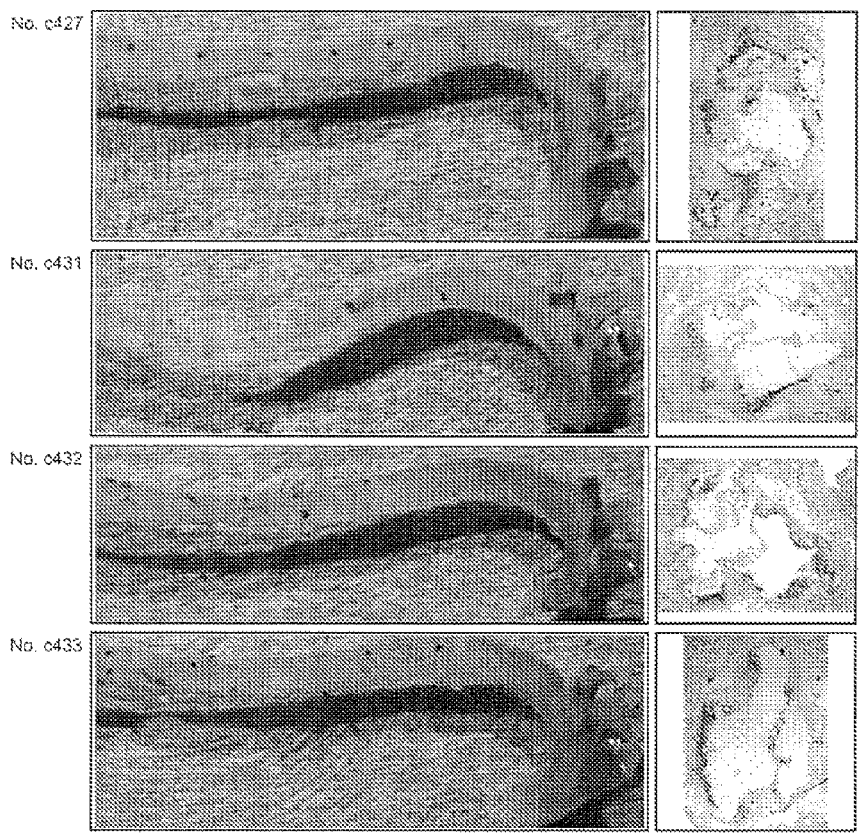
FIGS. 9B and 9C are photomicrographs of ApoE−/− illustrating atherosclerosis lesions in the aorta (left) and aortic valves (right) of male and female mice, respectively.
Figure 9C:
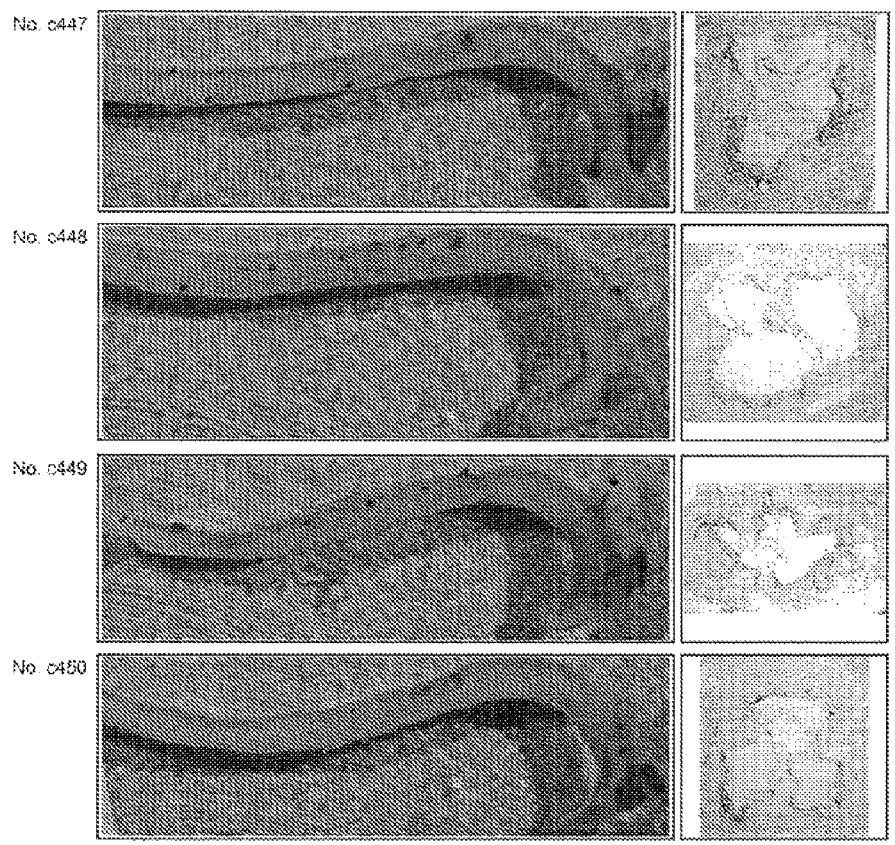
Figure 10A:
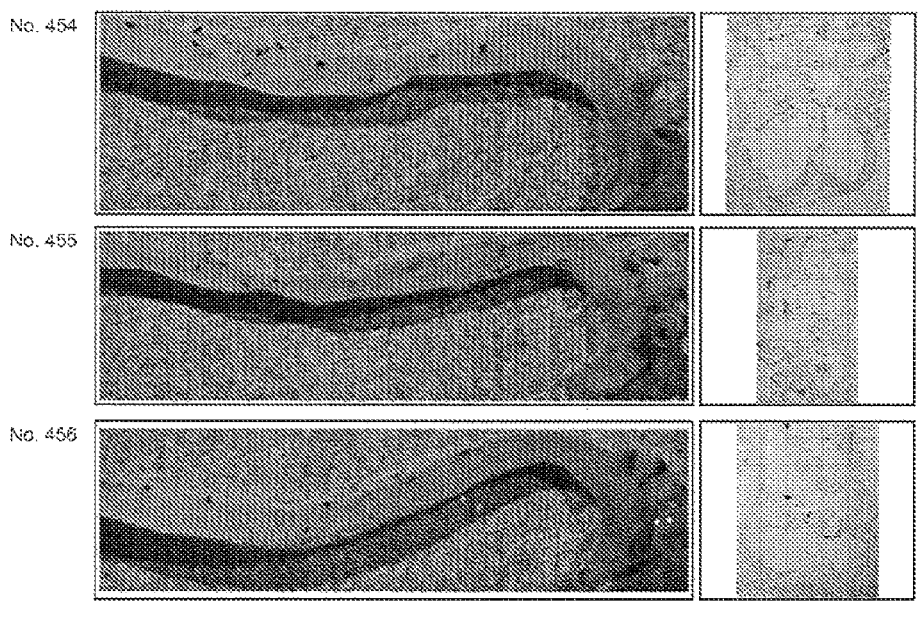
FIGS. 10A and 10B are photomicrographs of the aorta (left) and aortic valves (right) of male and female ApoE−/− mice, respectively, illustrating the effect of rhATF vaccination.
Figure 10B:
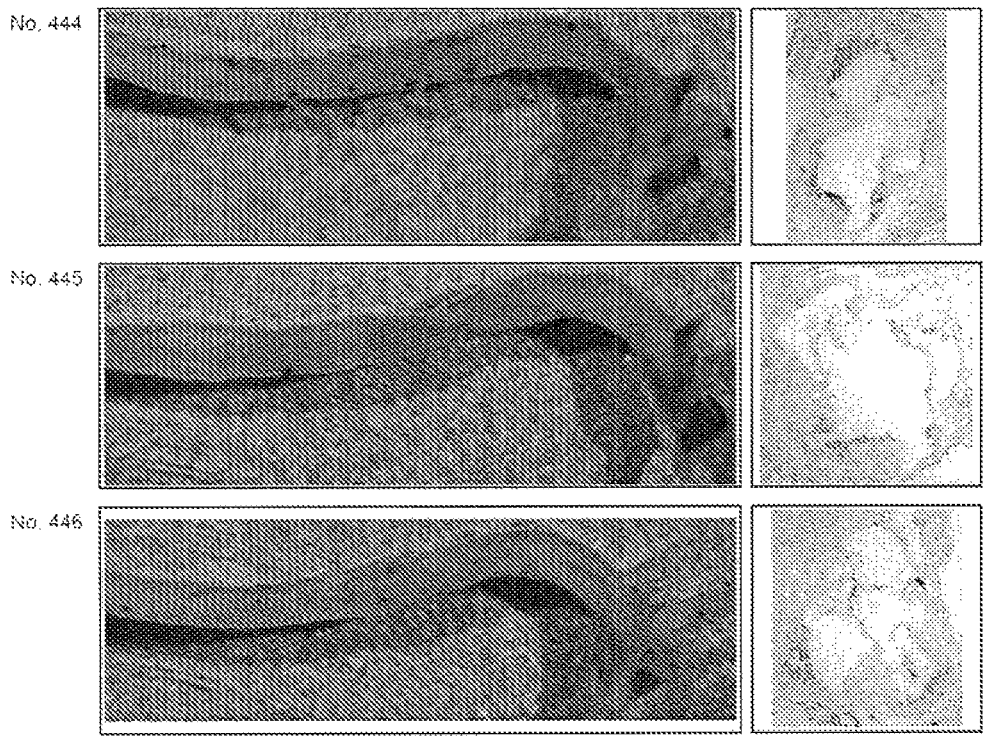
Figure 10C:
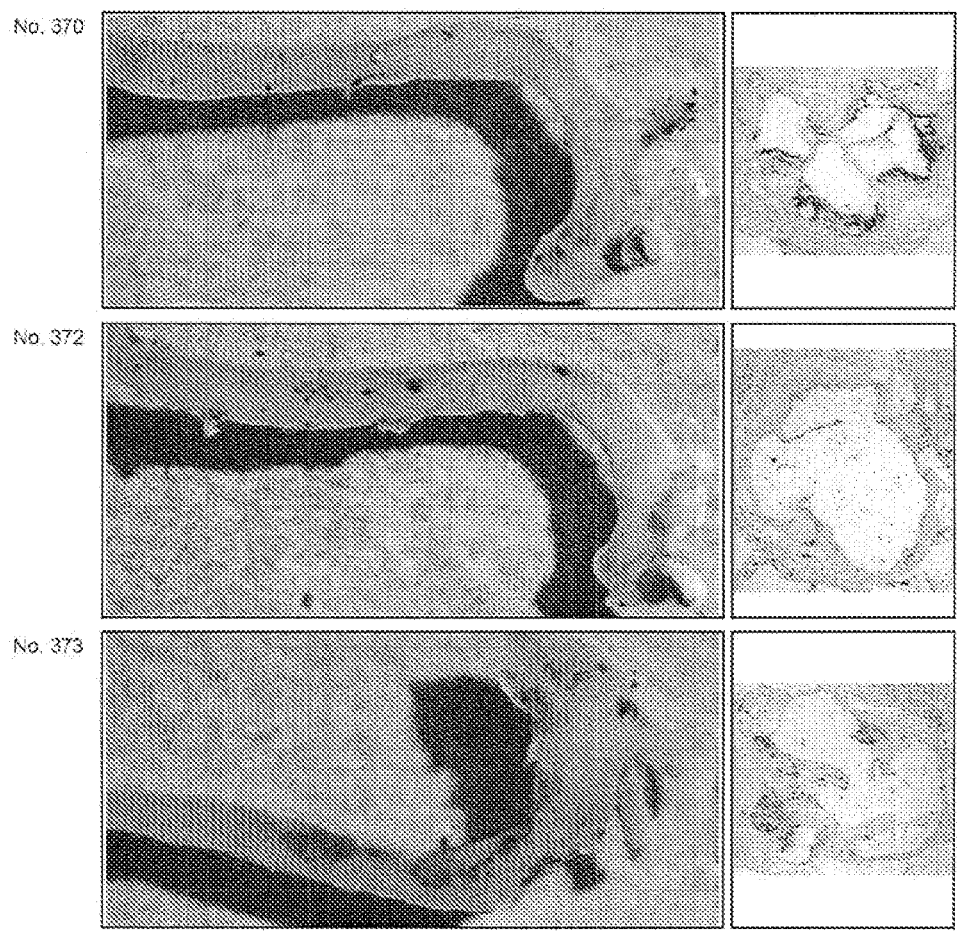
FIGS. 10C and 10D are photomicrographs of the aorta (left) and aortic valves (right) of male and female ApoE−/− mice, respectively, illustrating the effect of rhATF administered intravenously.
Figure 10D:
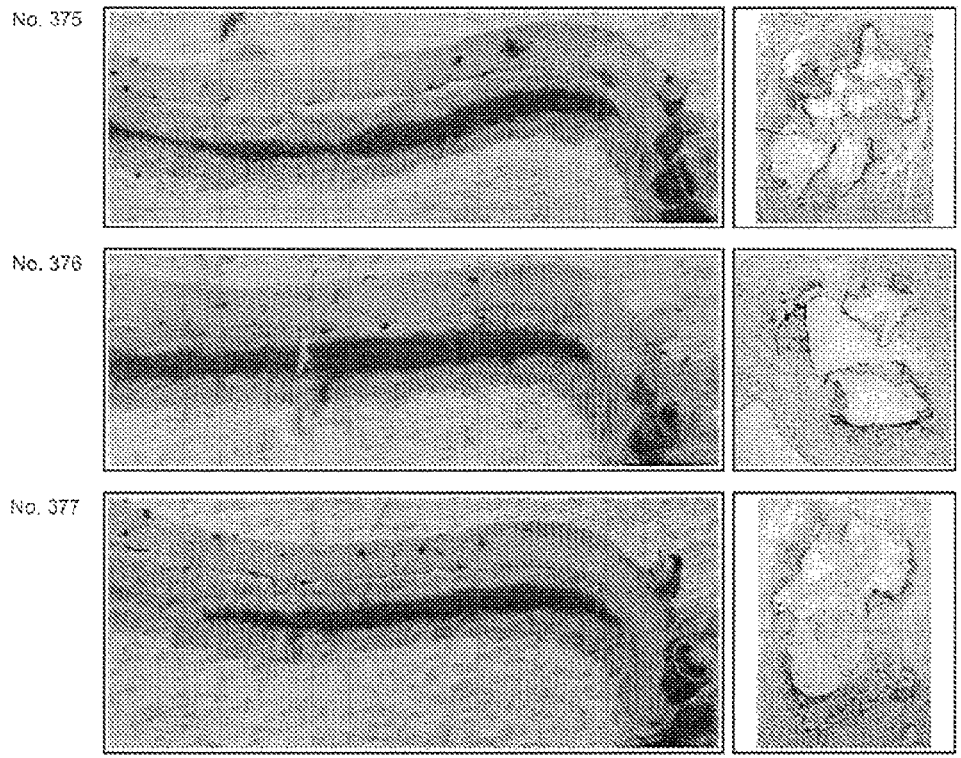
Figure 10E:
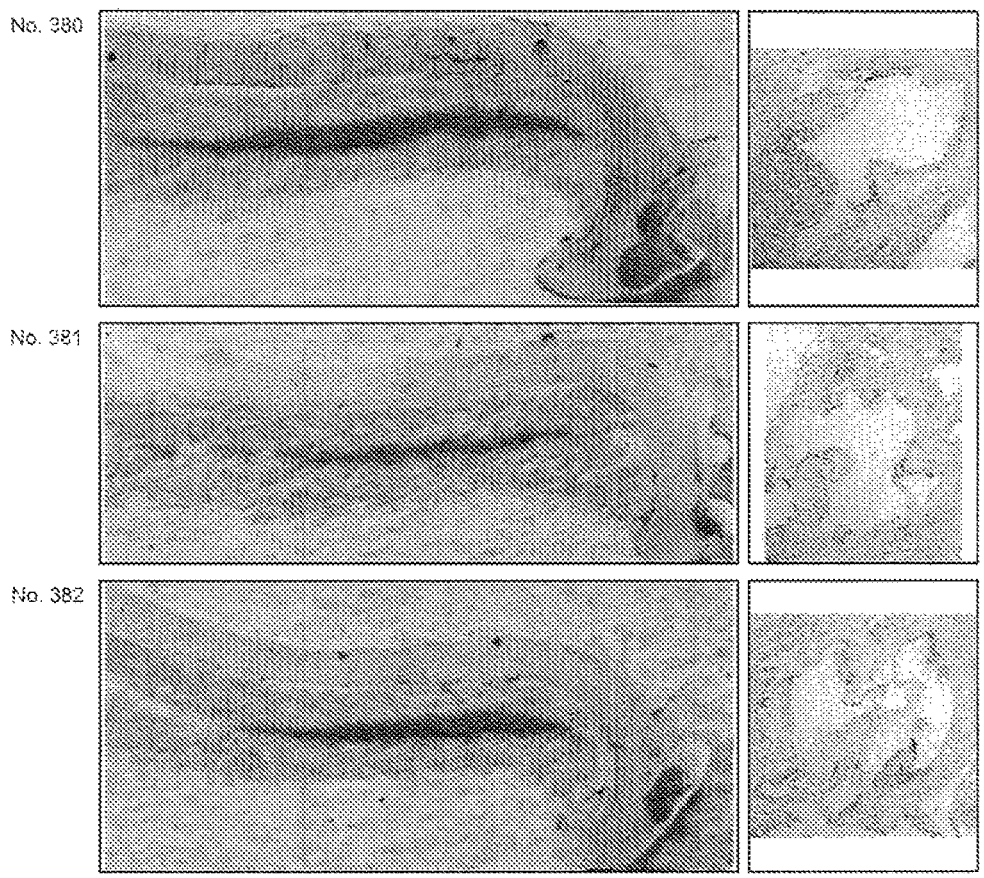
FIGS. 10E and 10F are photomicrographs of the aorta (left) and aortic valves (right) of male and female ApoE−/− mice, respectively, illustrating the effect of rhATF administered subcutaneously.
Figure 10F:
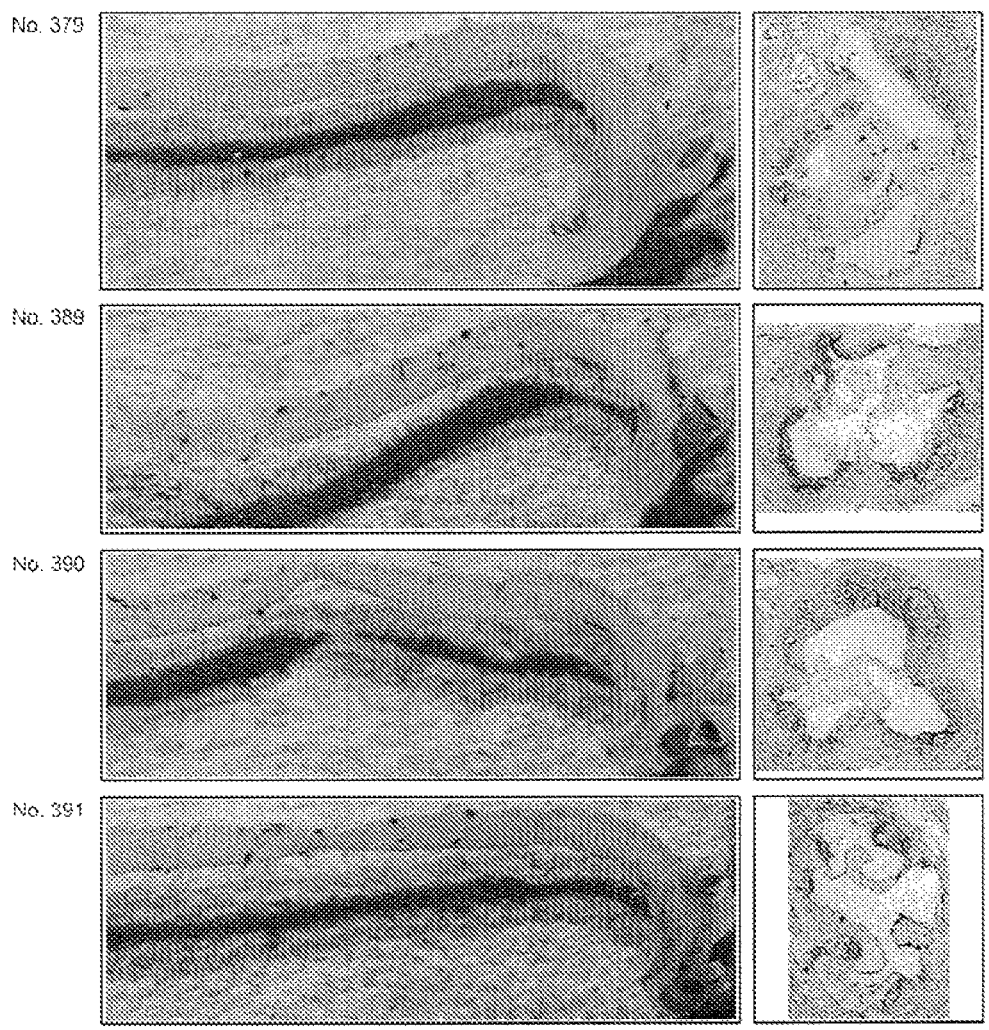

The ATF polypeptides used in the method described herein can be chimeric, i.e., they can include ATF fragments from different species. One exemplary chimeric ATF is an ATF from one species with its native receptor binding loop being replaced with a receptor binding loop from another species. A "receptor binding loop" of an ATF is the domain that directly binds to uPAR. It is usually located in close proximity to the N-terminal end of an ATF. Exemplary receptor binding loops of rabbit, human, and mouse are shown in FIGS. 1 and 2. Skilled practitioners can easily determine the receptor binding loop of an ATF by comparing the amino acid sequence of an ATF having an unknown receptor binding loop to that of an ATF having a known receptor binding loop, e.g., a human ATF or a mouse ATF.

A chimeric ATF can be a human ATF with its receptor binding loop (VSNKYFSIHW) (SEQ ID NO:12) being substituted with a receptor binding loop from another species, e.g., mouse (VSYKYFSRIRR) (SEQ ID NO:13), rat (VSYKYFSSIRR) (SEQ ID NO:14), cow (VTYKYFSNIQR) (SEQ ID NO:15), pig (VSYKYFSNIQR) (SEQ ID NO:16), rabbit (VTYKYFSNIWR) (SEQ ID NO:17) or chicken (ITYRFFSQIKR) (SEQ ID NO:18).

In addition to the full length ATFs described above, ATF polypeptides include fragments of these ATFs. An ATF fragment is a fragment able to bind to uPAR or to raise an immune response after introduction into an animal. Alternatively or in addition, they can contain an MHC Class II binding domain so that it is capable of inducing a T cell response. These MHC Class II binding domain can be predicted by methods known in the art. See Singh et al., *Bioinformatics*, 17(12):1236-37. Another exemplary ATF fragment includes an antibody epitope such that it induces antibody reactions when administered to a patient. Peptides having more than 8 amino acid residues are usually capable of inducing antibody responses.

Without intending to be bound by theory, an ATF polypeptide may function through either or both of two mechanisms to treat atherosclerosis. First, an ATF polypeptide may compete against endogenous uPA to bind to uPAR, thus blocking uPA-uPAR interaction. Such interaction may be important in development of atherosclerosis. Second, an ATF polypeptide may act as an antigen to induce immune responses, which result in anti-atherosclerosis effects. For example, the anti-ATF antibodies induced by ATF polypeptides may prevent endogenous uPA from binding to uPAR. T cell responses induced by ATF may also play a role in the anti-atherosclerosis effect of ATF.

b. Preparation of ATF Polypeptides

An ATF polypeptide can be produced by recombinant technologies or isolated from natural sources. For example, it can be prepared from a urokinase following the method described in Stoppelli et al., Proc. Natl. Acad. Sci., 82:4939-4943 (1985). An ATF fragment can be produced by recombinant technologies or synthesized. Also contemplated are ATF polypeptides that are partially natural and partially synthetic.

An ATF polypeptide can be modified to enhance its half-life in a patient. In one example, the polypeptide is coupled (e.g., conjugated or fused) with an agent (e.g., PEG or albumin) that is capable of extending its half-life by method know to those of skill in the art.

In another example, an ATF polypeptide can be chemically modified by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues can be modified by the formation of heterocyclic condensation products with reagents such as 2,3-butanedione, phenylglyoxal and glyoxal. The carboxyl group can be modified by carbodiimide activation via o-acylisourea formation followed by subsequent derivatization, for example, to a corresponding amide. Sulfhydryl groups can be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues can be modified by, for example, oxidation with N-bromosuccinimide or alkylation of the indole ring with 2-hydroxy-5-nitrobenzyl bromide or sulphonyl halides. Tryosine residues can be altered by nitration with tetranitromethane to form a 3-nitrotyrosine derivative. Modification of the imidazole ring of a histidine residue can be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

c. Preparation of Pharmaceutical Compositions Containing ATF Polypeptides

The ATF polypeptides can be formulated as pharmaceutical compositions, e.g., immunogenic compositions. In one example, the composition includes a pharmaceutically acceptable carrier, diluent, excipient or auxiliary. "Acceptable" means that the carrier, diluent, excipient or auxiliary is compatible with the active ingredient of the composition (and preferably, capable of stabilizing the active ingredient) and not deleterious to the subject to be treated. One or more solubilizing agents can be utilized as the pharmaceutical carrier. Examples of other carriers include colloidal silicon oxide, magnesium stearate, cellulose, sodium lauryl sulfate, and D&C Yellow #10.

In another example, the compositions containing one or more ATF polypeptides can further include an adjuvant, e.g., a lecithin, an oil, a surfactant, or a combination therefore. A preferred adjuvant contains an aqueous carrier solution, for example, phosphate-buffered saline (PBS) (e.g., Dulbecco PBS).

The compositions can contain a lecithin, e.g., from about 0.25% to about 12.5% v/v, more preferably from about 0.5% to about 5%, and most preferably from about 0.5% to about 1.25% v/v, or with an oil at from about 1% to about 23% v/v, more preferably from about 3.5% to about 10% and most preferably about 4.5%. The compositions can contain an amphiphilic surfactant, e.g., from about 1.5% to about 6% v/v, more preferably from about 1.5% to about 4% and most preferably about 2% v/v.

The adjuvants used in the above-mentioned compositions can include more than one component. In one example, the adjuvant can include two amphiphilic surfactants, e.g., TWEEN™ and SPAN™ surfactants, of which one predominantly in the aqueous phase (e.g., TWEEN 80™) of the pharmaceutical composition and one in the oil phase (e.g., SPAN 80™). When TWEEN 80™ and SPAN 80™ are used as surfactants, the concentration of TWEEN 80™ is typically about 1½ to about 3 times as high as the concentration of SPAN 80™, e.g., about 2 times. In another example, the adjuvant contains a mixture of a lecithin and an oil in DRAKEOL™ 5 Lt Mineral Oil. Lecithin can be obtained from Central Soya, Fort Wayne, Ind. See also U.S. Pat. No. 5,084,269, which discusses adjuvant compositions. TWEEN™ and SPAN™ surfactants can be obtained from Van Waters and Rogers, Omaha, Nebr.

Adjuvants known in the art, for example, oil emulsions, aluminum hydroxide, muramyl dipeptides, zinc calcium hydroxide, pyridine, aluminum hydroxide, oils and saponins can be used in formulating the above-described pharmaceutical composition.

The pharmaceutical composition comprising an ATF polypeptide can be manufactured by means of conventional mixing, dissolving, granulating, dragee-making, levigating, emulsifying, encapsulating, entrapping or lyophilizing processes.

d. Administration of Pharmaceutical Compositions Containing ATF Polypeptides

Conventional methods, known to medical practitioners, can be used to administer the pharmaceutical compositions described herein to a patient. For example, the compositions can be administered, e.g., orally, subcutaneously, intravenously, or intramuscularly, using standard methods. In general, compositions described throughout the specification can be administered at least once per day, e.g., twice, three times, or more, per day, for at least one day, e.g., 2 days, 3 days, 5 days, 1 week, 2 weeks, 1 month, 1 year, or longer. The compositions can be administered to the patient via injectable depot routes of administration such as by using 1-, 3-, or 6-month depot injectable or biodegradable materials and methods. The compositions can be administered prophylactically, e.g., at regular intervals, to patients who are at risk for developing atherosclerosis. The compositions can be administered, e.g., once a day, e.g., two times within one to two months, before and/or after development of atherosclerosis in the patient.

Injectable formulations of the compositions can contain various carriers such as vegetable oils, dimethylacetamide, dimethylformamide, ethyl lactate, ethyl carbonate, isopropyl myristate, ethanol, polyols (glycerol, prolylene glycol, liquid polyethylene glycol, and the like). For intravenous injections, water soluble versions of the compounds can administered by the drip method, whereby a pharmaceutical formulation containing the polypeptide (ATF or its fragment) and a physiologically acceptable excipient is infused. Physiologically acceptable excipients can include, for example, 5% dextrose, 0.9% saline, Ringer's solution or other suitable excipients. Alternatively, the proteins can be in powder form for constitution with a suitable vehicle, e.g., sterile pyrogen-free water, before use.

The compositions can be formulated as a depot preparation. Such long acting formulations can be administered by implantation (for example subcutaneously or intramuscularly) or by intramuscular injection. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

The compositions can be delivered orally. A solid formulation for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microglycolate, and alginic acid. Tablet binders that can be used include acacia, methylcellulose, sodium carboxymethylcellulose, polyvinylpyrrolidone (Povidone™), hydroxypropyl methylcellulose, sucrose, starch, and ethylcellulose. Lubricants that can be used include magnesium stearates, stearic acid, silicone fluid, talc, waxes, oils, and colloidal silica. This solid formulation can be designed such that the composition is released in the intestine. For example, the composition is confined in a solid sub-unit or a capsule compartment that have respectively a matrix or a wall or a closure comprising an enteric polymer which dissolves or disperses at the pH of the small or large intestine to release the drug substance in the intestine. Suitable such polymers have been described above, for example with reference to U.S. Pat. No. 5,705,189.

Other pharmaceutical delivery systems can be employed. Liposomes and emulsions are well known examples of delivery vehicles that can be used to deliver a polypeptide-containing composition. Certain organic solvents such as dimethylsulfoxide also can be employed, although usually at the cost of greater toxicity. Additionally, the composition can be delivered using a sustained-release system, such as semipermeable matrices of solid polymers containing the composition. Various sustained-release materials have been established and are well known by those skilled in the art. Sustained-release capsules can, depending on their chemical nature, release the active ingredient of the composition, i.e., ATF or its fragment, for a few weeks up to over 100 days.

The composition can also be administered by inhalation. By "inhalation" is meant intranasal and oral inhalation administration. Appropriate dosage forms for such administration, such as an aerosol formulation or a metered dose inhaler, can be prepared by conventional techniques.

Determination of an effective amount of the composition for administration is well within the capabilities of those skilled in the art, especially in light of the detailed disclosure provided herein. An effective amount of the composition is an amount that, when administered as described above, is capable of treating atherosclerosis in a patient, i.e., relieving the symptoms of atherosclerosis, reversing, ameliorating, or inhibiting the progress of atherosclerosis, and/or preventing the formation of atheromatous plaque in a patient.

Skilled practitioners will appreciate that an effective dose can be estimated initially from in vitro assays. For example, a dose can be formulated in atherosclerosis animal models, such as balloon injury rabbit model or ApoE−/− mouse model, to achieve an anti-atherosclerosis effect. Skilled practitioner can readily optimize administration to all animal species based on results described herein. Dosage amount and interval can be adjusted individually. For example, a composition containing 40-100 mg ATF and optionally, an adjuvant, can be administered intravenously to a human patient two times within one to months, or three times within two to three months. Booster administration can be given periodically thereafter if the titer of anti-ATF antibodies in that human patient is lower than 1:10,000.

The composition can be administered to a patient one or more times before and/or after atherosclerosis development. "Before atherosclerosis development" means that no atheromatous plaques are detectable in the patient by routine medical procedures. "After atherosclerosis development" means that detectable atheromatous plaques have been formed in the patient, or that the patient is exhibiting or has exhibited atherosclerotic symptoms. When the composition is administered to a patient multiple times, different delivery routes can be used in different times of administrations.

2. Treating Atherosclerosis with Anti-uPAR Antibodies

Methods described herein can include administering to a patient an antibody that specifically binds to uPAR. Anti-uPAR antibodies include, e.g., polyclonal antibodies, monoclonal antibodies, antibody fragments (e.g., single chain antibodies or Fab'), chimeric antibodies, and humanized antibodies. Exemplary anti-uPAR antibodies are those that target uPA binding sites in uPAR.

a. Antigens Used for Making Anti-uPAR Antibodies

A full-length uPAR polypeptide can be used as an antigen to produce the anti-uPAR antibodies. One example is human uPAR, the amino acid sequence (SEQ ID NO:8) of which is shown in FIG. 3. The uPAR can be purified from natural sources or generated by recombinant technologies. Alternatively, it can be a combination of both natural and synthetic stretches of amino acids A fragment of uPAR can be used as an antigen to induce anti-uPAR antibodies. uPAR fragments can include at least 8 amino acid residues. Alternatively or in addition, they can include at least one uPA binding site. One exemplary uPAR fragment is a 15-aa fragment containing at least one amino acid residue that directly interacts with uPA. The amino acid residues of uPAR for interacting directly with uPA have been determined in some uPAR polypeptides, e.g., human uPAR. Human uPAR includes three domains (Domain I, Domain II, and Domain III) that interact with human uPA (its ATF region). See Ploug et al., *Biochem. Soc. Trans.*, 30:177-183 (2002). Based on the three-dimensional structure of the rhATF-uPAR complex described in Huai, et al., Science 311: 656-659 (2006), the following uPAR amino residues are those that directly bind to human ATF: T8, R25, V29, L31, L40, R53, L55, Y57, L66, and E68 (in Domain I); R137, K139, R142, H143, R145, and H166 (in Domain II); and H251, L252, D254, and A255 (in Domain III). The uPA-interacting amino acid residues in another uPAR can be determined by comparing the structure of a uPAR with known uPA binding sites (e.g., human uPAR) to a uPAR with unknown uPA binding sites.

b. Preparation of Anti-uPAR Antibodies

Methods of making monoclonal and polyclonal antibodies and fragments thereof in animals are known in the art. See, for example, Harlow and Lane, (1988) Antibodies: A Laboratory Manual, Cold Spring Harbor Laboratory, New York. The term "antibody" includes intact molecules as well as fragments thereof, such as Fab, F(ab')$_2$, Fv, scFv (single chain antibody), and dAb (domain antibody; Ward, et. al. (1989) Nature, 341, 544).

In general, to produce antibodies against a polypeptide, the polypeptide can be coupled to a carrier protein, such as KLH, mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a polypeptide of this invention, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo. The ability to produce high titers of monoclonal antibodies in vivo makes it a particularly useful method of production.

Alternatively or in addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946, 778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, F(ab')$_2$ fragments that can be produced by pepsin digestion of an antibody molecule, and Fab fragments that can be generated by reducing the disulfide bridges of F(ab')$_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

c. Preparation and Administration of Pharmaceutical Compositions Containing Anti-uPAR Antibodies The above-mentioned anti-uPAR antibodies can be formulated as pharmaceutical compositions and administered to a patient following the methods described above.

Without intending to be bound by theory, anti-uPAR antibodies can be effective in treating atherosclerosis by interrupting the binding between uPA and uPAR and thus are effective in treating atherosclerosis.

3. Treating Atherosclerosis with Other Agents

In addition to ATF polypeptides and anti-uPAR antibodies, other agents, such as those capable of blocking the interaction between uPA and uPAR, can be used in methods described herein. Agents capable of blocking uPA-uPAR binding include, but not limited to, anti-ATF antibodies, uPAR polypeptides, nucleic acids expressing ATF polypeptides or uPAR polypeptides, small organic compounds (e.g., non-peptide molecules). Details for using these agents for treating atherosclerosis are typically the same as described above.

In general, small organic compounds useful for the methods described herein have a molecule weight of less than 2500 Daltons (Da). The small molecule can be, e.g., from at least about 100 Da to about 2000 Da. These molecules are capable of binding to either uPA-binding sites in uPAR (e.g., Domain I, Domain II, or Domain III of uPAR) or uPAR-binding sites in uPA (e.g., ATF or receptor binding loop) with an affinity constant of at least about $2 \times 10^4$ $M^{-1}$, e.g., at least about $10^5$ $M^{-1}$, at least about $10^6$ $M^{-1}$, at least about $10^7$ $M^{-1}$, and at least about $10^8$ $M^{-1}$.

An agent capable of blocking the interaction between uPA and uPAR can be identified using methods known in the art, e.g., a high-throughput screening. In one example, a first polypeptide and a second polypeptide is provided. The first polypeptide can be uPA or a fragment thereof capable of binding to uPAR (e.g., ATF or the receptor binding loop). The second polypeptide can be uPAR or a fragment thereof capable of binding to uPA (e.g., a fragment including one or more ATF binding sites). Either the first polypeptide or the second peptide can be labeled. The first polypeptide, the second polypeptide, and a candidate agent are contacted with each other. The amount of label bound to the unlabeled polypeptide is determined. A reduction of protein-protein interaction between the first and the second polypeptides as assessed by label bound is indicative of the usefulness of the agent in inhibiting protein-protein interaction between uPA and uPAR.

By high-throughput screening is meant that the method can be used to screen a large number of candidate agents easily and quickly. In one example, a plurality of candidate agents are contacted with the first and second polypeptides. The different candidate agents can be contacted with the other polypeptides in groups or separately. Each of the candidate agents can be contacted with both the first polypeptide and the second polypeptide in separate wells. For example, the method can screen libraries of potential agents. Libraries are meant to include, e.g., natural product libraries, organic chemical libraries, combinatorial chemical libraries, peptide libraries, and modified peptide libraries, including, e.g., D-amino acids, unconventional amino acids, or N-substituted amino acids. The libraries can be in a form compatible with screening in multiwell plates, e.g., 96-well plates. The assay is particularly useful for automated execution in a multiplewell format in which many of the steps are controlled by computer and carried out by robotic equipment. The libraries can also be used in other formats, e.g., synthetic chemical libraries affixed to a solid support and available for lease into microdroplets.

Anti-ATF and anti-uPAR antibodies are also useful for detecting or purifying uPA and uPAR, respectively. Methods for using antibodies for the detection and/or purification of proteins are well known to those skilled practitioners.

EXAMPLES

The specific examples below are to be construed as merely illustrative, and not limitative of the remainder of the disclosure in any way whatsoever. Further, any mechanism proposed below does not in any way restrict the scope of the claimed invention.

Example 1

Preparation of Recombinant Human ATF (rhATF)

Human ATF-encoding cDNA was cloned from endothelial cells of human umbilical vein by RT-PCR, inserted into pET-29a(+) vector, and expressed in *E. coli* BL21(DE3). The expressed rhATF was then refolded and purified from the bacterial culture media to a homogeneity greater than 95% using CM-cellulose and Superdex G-75 columns. The rhATF thus obtained was capable of blocking uPA-uPAR binding. See Wang et al., *Journal of Nanjing University*, 40(1):66-74 (2004).

Example 2

Atherosclerotic Lesion Formation in Injured Rabbit Aorta

Twelve healthy male New Zealand white rabbits (2.8-3.5 kg) were used in this example. After anesthetized with pentobarbital sodium (30 mg/kg), the aortic walls of the rabbits were surgically opened wide enough to insert a 4F Fogarty balloon catheter from the left femoral artery to the abdominal aorta (about 20 cm). The balloon was then inflated with 0.85 ml saline and the catheter gently retreated for 10 cm. This procedure was repeated for four times to ensure that the arterial walls were damaged completely. Then the catheter was removed and the incision closed. 200,000 IU of penicillin mixed with saline were administered to each rabbit to prevent infection.

Immediately after the just-described surgery, the rabbits were fed with high fat diet (HFD) (a diet of chow supplemented with 1% cholesterol, 5% lard, and 7.5% vitelline powder) for 7, 10, or 14 days. These animals were then sacrificed and examined for the formation of atherosclerosis lesions in their injured aorta following the procedures described below. The rabbits were first deeply anesthetized to remove blood from their carotid artery and then sacrificed, their aorta (from the aortic arch to the femoral bifurcation) being excised, cut to open, and stained with Oil Red O (ORO). The percentages of the injured areas were determined using Image-Pro Plus 5.1 (MediaCybernetics, Inc.).

Figure 4:
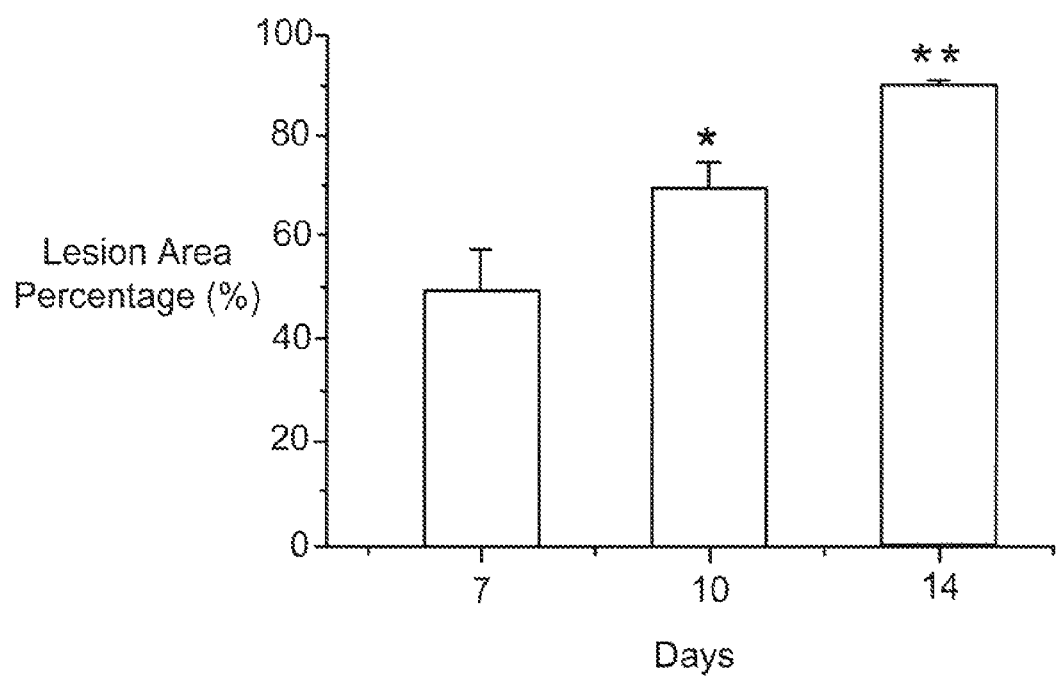
FIG. 4 is a bar graph that depicts a time course of atherosclerotic lesion formation in rabbits subjected to balloon aortic injury.

Rabbits fed with HFD for 7 days showed clear atherosclerotic lesion formation in their injured aorta. See FIG. 4.

Example 3

Preventing Atherosclerotic Lesion Formation in Injured Rabbit Aorta with rhATF Administered Intravenously After balloon aorta injury described above, rabbits in a testing group were intravenously administered with 1 mg rhATF per animal immediately after the balloon aorta injury, once a day for 7 days. Rabbits in a control group were administered with PBS instead of rhATF. During this period of time, all of the rabbits were fed with HFD. At day 7, they were sacrificed to examine the formation of atherosclerotic lesions in the injured aorta.

Figure 5:
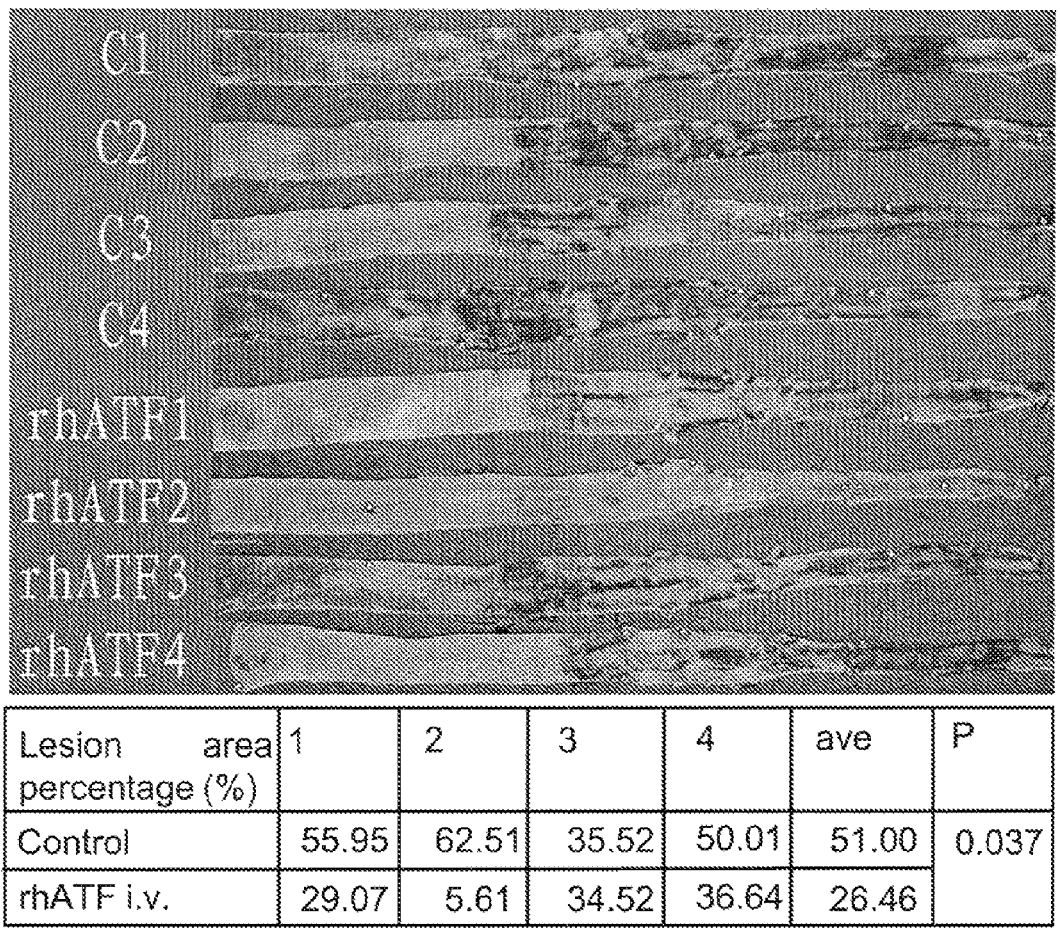
FIG. 5 is a photomicrograph of rabbit aorta illustrating the anti-atherosclerotic effect of rhATF administered intravenously.

Results obtained in this example were shown in FIG. 5. Compared to the rabbits treated with PBS, the rabbits treated with rhATF showed about 50% reduction in atherosclerotic lesion formation in their injured aorta.

Example 4

Preventing Atherosclerosis Lesion Formation in Injured Rabbit Aorta with rhATF Vaccination Rabbits were immunized twice with rhATF mixed with CFA, 2 mg rhTAF for each rabbit and once every other week. At day 7 after the second round of immunization, the anti-ATF antibody titers in each immunized animal were determined using ELISA.

Figure 11:
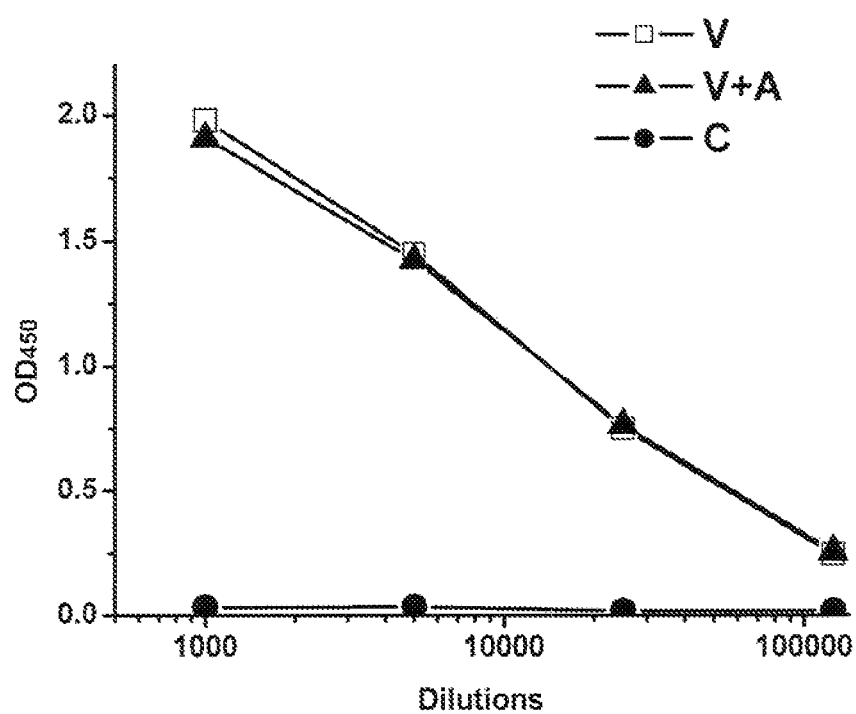
FIG. 11 is a graph that shows the anti-rhATF antibody titers in rabbits treated with rhATF.

Briefly, an ELISA plate was coated with rhATF (1 µg/well) overnight at 4° C. and then blocked with PBS containing 0.1% tween-20 and 5% milk for 2 hrs at room temperature. Immune sera obtained from the immunized animals were subjected to serial dilution. The diluted sera and a control serum were added to separate wells and incubated for another 2 hrs. HRP conjugated donkey anti-rabbit IgG antibodies (1:10000, Pierce) were added to these wells, 100 µl in each well, and incubated for 30 minutes. 3,3'5,5'-tetramethylbenzidine base (TMB) solution was then added to each well and the optical density was measured using an ELISA plate reader at the wavelength of 450 nm. The antibody titers were determine as the highest degree of dilution that provides an absorbance at 450 nm 4 times greatest than the control serum. FIG. 11 shows that the anti-rhATF antibodies in rhATF vaccinated rabbit was higher than 1:100,000.

Figure 6:
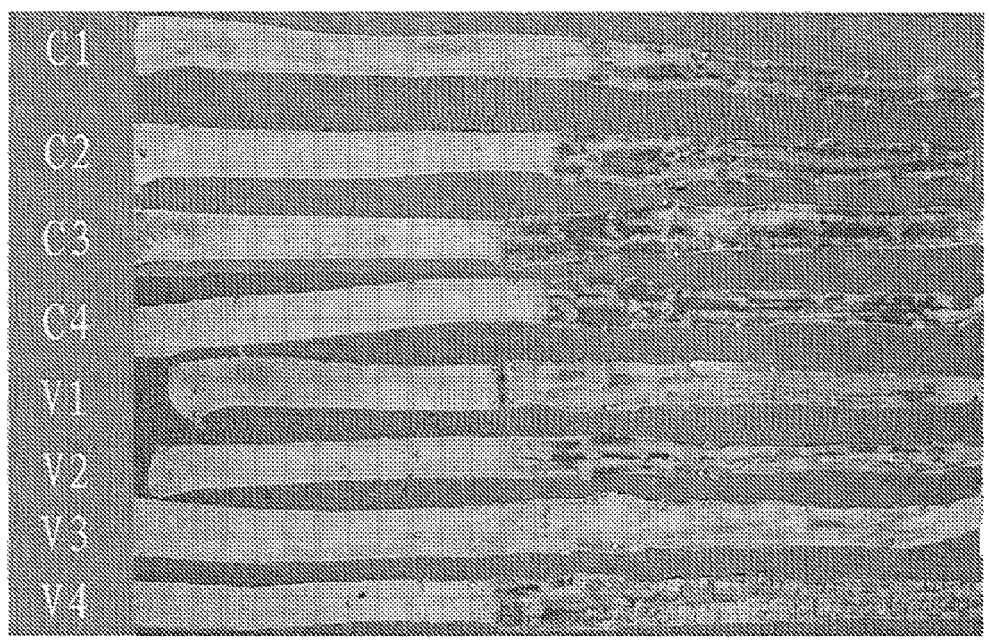
FIG. 6 is a photomicrograph of rabbit aorta illustrating the anti-atherosclerotic effect of rhATF vaccination.

After the antibody titers were determined, these vaccinated rabbits were subjected to the surgery of balloon aorta injury, fed with HFD for 7 days and then sacrificed, the formation of atherosclerotic lesions in their injured aorta being examined. Results thus obtained were shown in FIG. 6. About 50% reduction of atherosclerotic lesions was observed in rhATF vaccinated rabbits, compared to the rabbits treated with PBS.

Example 5

Treating Rabbits with Anti-rhATF Polyclonal Antibody Subcutaneously

Anti-rhATF polyclonal antibodies were purified from rabbits vaccinated with rhATF, using protein-A affinity column. Testing rabbits were treated with anti-rhATF polyclonal antibodies by subcutaneous injection for 4 consecutive weeks (10 mg per animal, once every week). Rabbits in a control group were treated with PBS instead. At day 3 after the treatment, the surgery of balloon aorta injury was performed to each rabbit. These animals were then fed with HFD for seven days and sacrificed to examine the formation of atherosclerotic lesions in their injured aorta.

Figure 7:
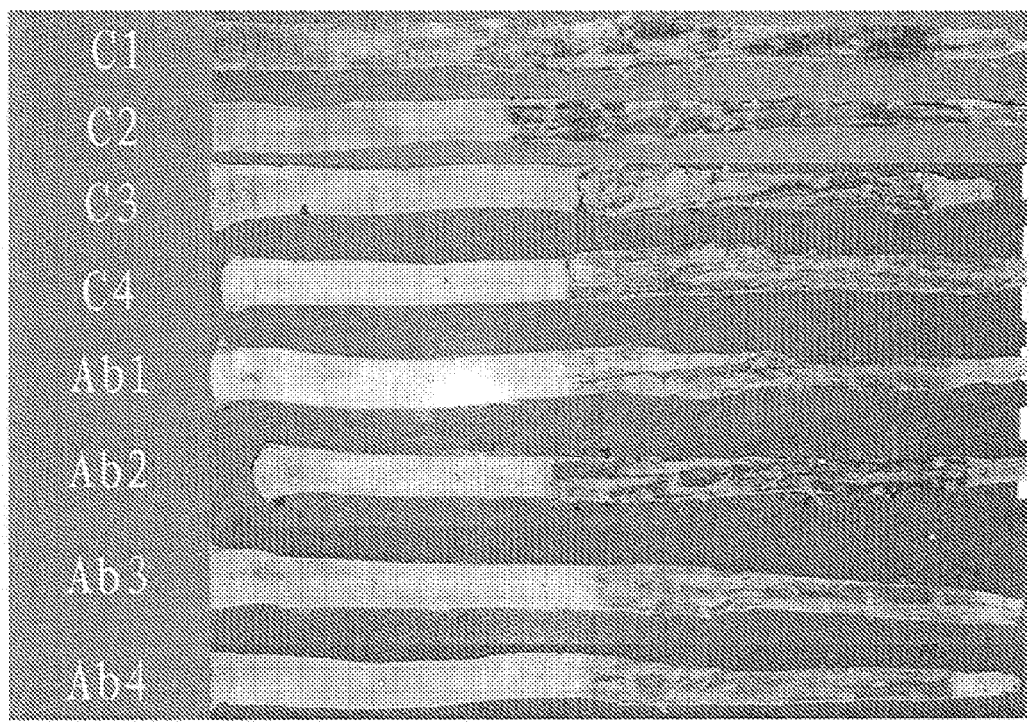
FIG. 7 is a photomicrograph of rabbit aorta illustrating the effect of polyclonal anti-rhATF antibodies administered subcutaneously.

As shown in FIG. 7, there was a reduction of atherosclerotic lesions in animals treated with anti-rhATF polyclonal antibodies. However, the reduction was not as significant as the rabbits treated with rhATF vaccination. See also FIG. 6. This result suggests that the full immune response, as opposed to just the antibody-mediated responses, induced by rhATF vaccination could be important for the anti-atherosclerosis effects.

Example 6

Treating Injured Rabbits with Both Intravenous Injection of rhATF and rhATF Vaccination Rabbits vaccinated with rhATF following the procedures described above were subjected to the surgery of balloon aorta injury after their anti-rhATF antibody titers were determined. These animals were then fed with HFD and intravenously injected with rhATF (1 mg per rabbit, once a way) for 7 days. At day 7, they were sacrificed and the formation of atherosclerotic lesions in their injured aorta examined.

Figure 8:
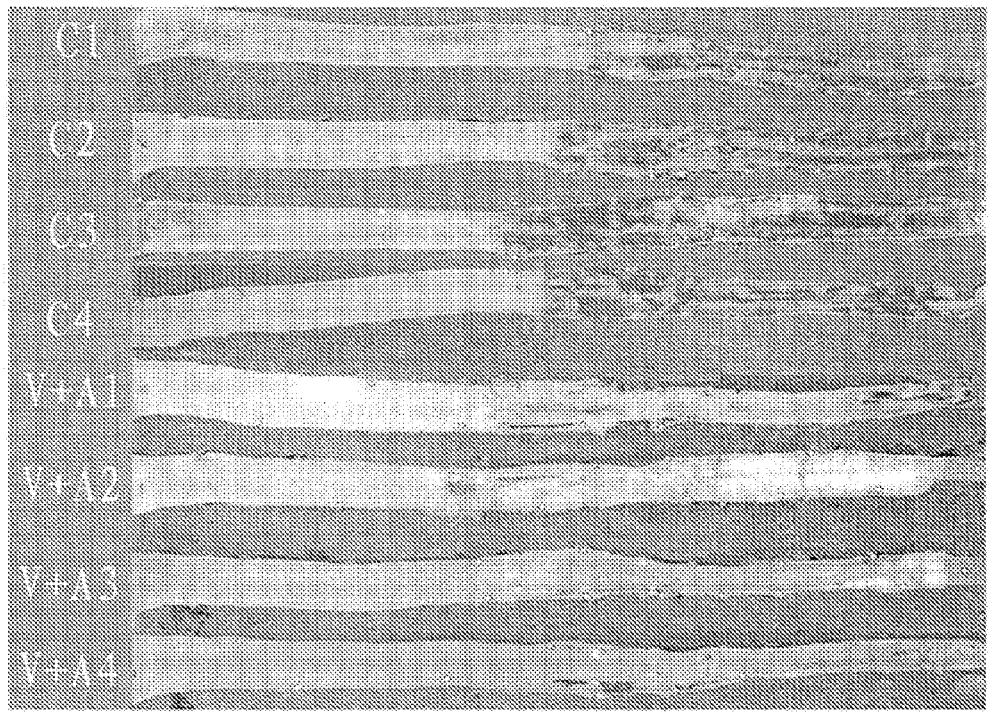
FIG. 8 is a photomicrograph of rabbit aorta illustrating the joint anti-atherosclerotic effect of rhATF vaccination and rhATF administered intravenously.

FIG. 8 shows that the formation of atherosclerotic lesions was significantly reduced in rabbits treated with rhATF intravenously and rhATF vaccination than in control rabbits (treated with PBS). This level of reduction is also significantly greater that that in rabbits treated with either rhATF intravenously or rhATF vaccination alone. See FIGS. 5 and 6.

Example 7

Treating Atherosclerosis in ApoE Deficient Mice

Male and female ApoE heterozygous mice with C57BL/6J background were obtained from the Jackson Laboratory (Bar Harbor, Me.). These mice were mated and maintained under specific pathogen-free conditions in static micro-isolator cages. The offspring of these mice was genotyped by PCR following the Jackson Laboratory method (see Underkoffler L A et al., *Biol Proced Online.* 2003; 5: 116-122) and ApoE-deficient mice (ApoE–/–) were selected based on the genotyping results. The ApoE–/– mice were maintained on 12-h dark/12-h light cycles in air conditioned rooms (20-22° C., 40-70% humidity) and access to diet and water ad labium.

ApoE–/– mice were sacrificed at the ages of 12, 16, 19.5, and 22 weeks to examine the formation of atherosclerosis lesions in their aorta following the procedures below. Each mouse was deeply anesthetized and its heart was gently perfused with PBS containing 0.38% trisodium citrate. Then the mouse was sacrificed and its aorta excised and stained with ORO. Cryostat sections of 5 µm were cut from the stained aorta and placed on gelatin-coated slides. These sections were analyzed under a microscope using Image-Pro Plus 5.1 described above. The ORO stained atherosclerosis area in aortic valves was specifically measured.

As shown in FIG. 9A, atherosclerotic lesions were formed in the aorta and aortic valves of the ApoE–/– mice at the age of 19.5 weeks.

At the age of 9 weeks, a randomly selected group of ApoE–/– mice (Group A) were vaccinated with rhATF (1 mg/ml, 0.2 ml per mouse) mixed with CFA once every week for two weeks. Determined by ELISA as described above, the anti-rhATF antibody titers in the vaccinated mice were higher than 1:100,000. See Table 1. The antibody titers were maintained at that level by additional vaccination until the age of 19.5 weeks. All vaccinated mice were sacrificed at the age of 19.5 weeks for examination of atherosclerotic lesions in their aorta and aortic valves.

TABLE 1

Serum Antigen Titer of ATF-Vaccinated ApoE Deficient Mice

| Age | Female | | | Male | | |
|---|---|---|---|---|---|---|
| (weeks) | 454 | 455 | 456 | 444 | 445 | 446 |
| 11 | 1:72900 | 1:218700 | 1:72900 | 1:24300 | 1:8100 | 1:218700 |
| 13 | 1:291600 | 1:72900 | 1:24300 | 1:145800 | 1:437400 | 1:291600 |
| 15 | 1:48600 | 1:72000 | 1:145800 | 1:291600 | 1:291600 | 1:291600 |
| 16 | 1:437400 | 1:291600 | NA | NA | NA | NA |
| 19.5 | 1:291600 | 1:437400 | 1:437400 | 1:437400 | 1:291600 | 1:437400 |

Note:
Mice vaccinated with ATF (0.2 ml per mouse, 0.5 mg/ml) started at week 9, once per week for two weeks. Due to the low titer of anti-rhTAF antibodies, mice 444 and mouse 445 were vaccinated one more time at the age of 11 weeks; mice 455 and 456 were further vaccinated at the age of 13 weeks; and mice 454 and 455 at the age of 15 weeks.

At the age of 12 weeks, ApoE−/− mice were randomly divided into two groups, each receiving (1) rhATF (2.8 μg per mouse daily) by intravenous injection (Group B) and (2) rhATF (2.8 μg per mouse daily) by subcutaneous injection (Group C), respectively, until the age of 19.5 weeks. All mice were then sacrificed for examination of atherosclerotic lesions in their aorta and aortic valves.

Results obtained from Group A, Group B, and Group C mice were shown in both Table 2 below and FIGS. 10A-10F. Clearly, the greatest anti-atherosclerosis effect was observed in Group A mice, which were treated with rhATP vaccination, compared to that in Group B mice, which were treated with intravenous injection of rhATF and in Group C mice, which were treated with subcutaneous injection. The reduction of atherosclerotic lesion formation in mice treated subcutaneously (Group C) was not as significant as that in mice treated intravenously (Group B). This result may due to the degradation or insufficient absorption of rhATF when injected subcutaneously.

In all of the three groups, the anti-atherosclerosis effects in male mice were greater than in female mice. This gender difference was consistent with the difference in atherosclerosis development between male and female ApoE−/− mice. See FIG. 10A. The same gender difference has also been observed in the rabbit balloon aorta injury model described above.

TABLE 2

Atherosclerotic Lesions Stained by ORO in Aortic Valves of Male ApoE Deficient Mice (age 19.5 weeks)

| The controls | c427 | c431 | c432 | c433 |
|---|---|---|---|---|
| Lesion area (μm²) | 2282.10 | 874.94 | 2301.39 | 1427.18 |
| Ave. lesion area (μm²) | 1721.40 ± 696.14 | | | |
| The group A | 454 | | 455 | 456 |
| Lesion area (μm²) | 53.22 | | 80.22 | 957.89 |
| Ave. lesion area (μm²) | 363.77 ± 514.68 (p = 0.03) | | | |
| The group B | 370 | | 372 | 373 |
| Lesion area (μm²) | 1562.96 | | 444.02 | 1592.26 |
| Ave. lesion area (μm²) | 1199.75 ± 654.64 (p = 0.16) | | | |
| The group C | 380 | | 381 | 382 |
| Lesion area (μm²) | 3381.12 | | 1072.50 | 534.00 |
| Ave. lesion area (μm²) | 1662.54 ± 1512.49 (p = 0.66) | | | |

Atherosclerotic Lesions Stained by ORO in Aortic Valves of Female ApoE Deficient M (age 19.5 weeks)

| The controls | c447 | c448 | c449 | C450 |
|---|---|---|---|---|
| Lesion area (μm²) | 2393.69 | 1729.21 | 5787.94 | 4659.37 |
| Ave. lesion area (μm²) | 3642.55 ± 1902.38 | | | |
| The group A | 444 | 445 | 446 | |
| Lesion area (μm²) | 3161.83 | 989.33 | 1415.16 | |
| Ave. lesion area (μm²) | 1855.44 ± 1151.23 (p = 0.18) | | | |
| The group B | 375 | 376 | 377 | |
| Lesion area (μm²) | 1732.80 | 2306.16 | 3316.04 | |
| Ave. lesion area (μm²) | 2451.67 ± 801.59 (p = 0.5) | | | |
| The group C | 379 | 389 | 390 | 391 |
| Lesion area (μm²) | 2201.86 | 3421.59 | 5747.19 | 1360.60 |
| Ave. lesion area (μm²) | 3182.81 ± 1907.51 (p = 0.74) | | | |

Example 8

Binding Assays between rhATF and Rabbit/Mouse uPAR

Rabbit or mouse peripheral blood mononuclear cells (PBMCs) were collected in 3.8% trisodium citrate and diluted with PBS (1:1). The diluted blood was then placed on top of a lymphocyte-isolated solution (Haoyang Biological Science and Technology Company, China) at a ratio of 2:1 (v/v) and centrifuged at 2000 rpm, 19° C. for 20 minutes. After centrifugation, the mononuclear layer was recovered from the gradient interface and washed twice with PBS. In order to remove any uPA that was bound to uPAR, the cells were incubated in 1 ml glycine-HCl (50 mM, pH 3.0) containing 0.1 M NaCl for 3 minutes at room temperature, followed by neutralization in 1 ml PBS.

After the acid treatment, the cells were washed four times with RPMI 1640 medium containing 0.1% BSA, and then incubated with 10 nM of $^{125}$I-rhATF in the same medium for 1.5 hr at 4° C. After removing unbound $^{125}$I-rhATF by centrifugation, the cells were washed with PBS for three times and measured with a gamma counter for radioactivity associated therewith.

Results obtained from the above described assays showed that $^{125}$I-rhATF could bind to rabbit uPAR, but not mouse uPAR. This result is consistent with the fact that rhATF is more structurally similar to rabbit ATF than to mouse ATF. As shown above, rhATF is effective in treating atherosclerosis in mice. This anti-atherosclerosis effect may be due to the ability of rhATF to induce antibodies that are cross reactive to both human and mouse uPAs (ATFs).

Example 9

Presence of uPA in Atherosclerotic Lesions

Atherosclerotic lesions in both rabbits and mice were induced following the methods described above. The tissue samples containing atherosclerotic lesions were weighed, grounded, and extracted using 2×SDS buffer and fractionated by electrophoresis using 10% polyacrylamide slab gels in the buffer system of Laemmli. Zymographic analysis was then performed according to a method described in Granelli-Piperno et al., *J. Exp. Med.*, 148:223-234 (1978) and modified in Vassalli et al., J. Exp. Med., 159:1653-68 (1984). In general, after electrophoresis, the gels were washed by agitation for 45 min. in 2.5% Triton X-100 and 1 hour in 0.1 Tris-HCl to remove SDS. Then, the gels were placed on an underlay consisting of 0.0125 g/ml agarose, 0.02 g/ml casein, and 10 mg/ml plasminogen and incubated at 37° C. overnight. The amount of uPA was semi-quantified according to the size of the lysis zone on the casein plate. See Li et al., Thrombosis Research, 103:221-232 (2001).

uPA was detected in the atherosclerotic lesions of ApoE−/− mice but not the mice treated with ATF vaccination. In the rabbit model, the levels of uPA were significantly reduced in the vaccinated animals compared to control animals. These results suggest that rhATF vaccination is effective in treating atherosclerosis by inhibiting the binding between uPA and its receptor uPAR.

Example 10

Studies on Side Effects of rhATF Intravenous Treatment and rhATF Vaccination

1. Levels of Serum uPA

The levels of serum uPA in rhATF vaccinated animals were determined following the just-described method. No significant changes of serum uPA were found between vaccinated animals and control animals, indicating that the rhATF vaccination did not affect the levels of uPA in blood.

2. Catalytic Activity of Urokinase

The effect of anti-rtATF antibodies on the catalytic activity of urokinase was examined next, using both S2444 and plasminogen as substrates. First, urokinase (10 nmol/L) was incubated with or without rabbit anti-rhATF polyclonal antibodies (3 µmol/L) or control rabbit antibodies (3 µmol/L) for 1 hour. The chromogenic substrate S2444 (0.3 mmol/L) was then added to the mixture. The reaction rate was measured by the linear optical density (O.D.) increase with time at 410 nm against a reference wavelength of 490 nm using a microtiter plate reader described in Liu, et al., Blood, 81:980-7 (1993).

Second, urokinase (0.5 nmol/L or 0.05 nmol/L), pretreated with anti-rhATF polyclonal antibodies or control rabbit IgG (3 µmol/L), was mixed with S2251 (0.3 mmol/L), plasminogen (2 µmol/L) and incubated for 1 hour at room temperature in 0.05 mol/L sodium phosphate, 0.15 mol/L NaCl, 0.2% BSA, 0.01% Tween 80, pH 7.8. The OD increase in the reaction mixture was measured as described above.

Figure 12:
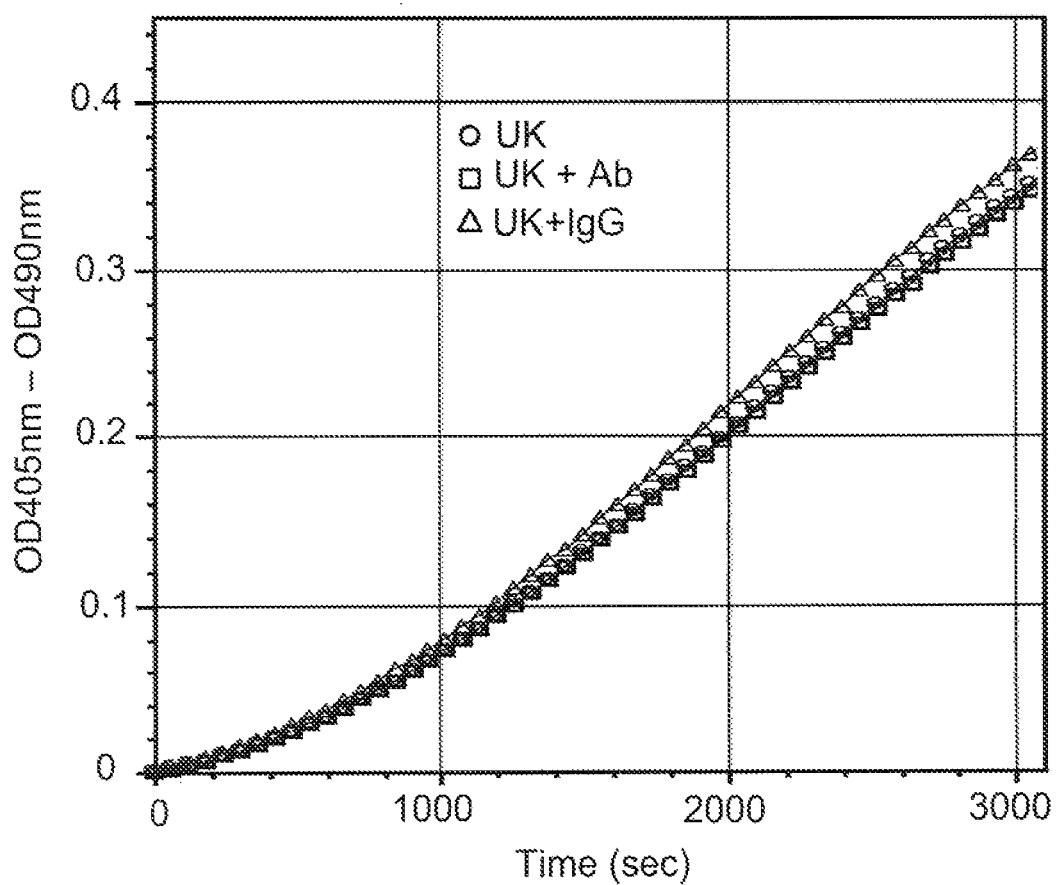
FIG. 12 is a graph that shows the effect of anti-rhATF antibodies on the plasminogen activation activity of urokinase.

Results from these experiments showed that rabbit anti-rhATF polyclonal antibody had no effect on the catalytic activity of urokinase against either S2444 or plasminogen. See Table 3 below and FIG. 12.

TABLE 3

Effect of Anti-rhATF Antibody (Ab) on Hydrolysis of Synthetic Substrate S2444 by Urokinase

| | Urokinase activity (nM) | |
| --- | --- | --- |
| | Without pre-incubation | Pre-incubation |
| Urokinase | 10.308 | 10.570 |
| Urokinase plus Ab | 10.527 | 10.938 |
| Urokinase plus IgG | 10.162 | 10.493 |

3. Hematological Analysis

Citrated blood was collected from rabbit or ApoE−/− mice either during treatment or at the time of sacrifice. The numbers and types of blood cells were measured using an automatic cell counter and results are shown in Tables 4-6. No obvious changes in hematological parameters were observed in rhATF treated animals.

TABLE 4

Rabbits Intravenously Administered with rhATF for Seven Days

| Number × $10^9$ | WBC | Lymph | Mid | Gran | Plt |
| --- | --- | --- | --- | --- | --- |
| Controls | 15.2 ± 5.9 | 7.0 ± 2.9 | 1.6 ± 0.7 | 6.7 ± 2.5 | 165 ± 38 |
| rhATF i.v. | 13.8 ± 1.9 | 7.0 ± 0.56 | 1.6 ± 0.5 | 5.2 ± 1.4 | 215 ± 17 |

WBC indicates white blood cell; Lymph, lymphocyte; Mid, middle cell; Gran, granulocyte; Plt, platelet; Data is expressed as mean ± SD of 4 rabbits in one group.

TABLE 5

Hematological Parameters of rhATF-Vaccinated Mice and Non-Vaccinated Controls

| | Female | | | | Male | | | |
| --- | --- | --- | --- | --- | --- | --- | --- | --- |
| | 444 | 445 | 446 | Controls(n = 5) | 454 | 455 | 456 | Controls(n = 4) |
| RBC(×$10^{12}$/L) | 7.19 | 9.17 | 6.89 | 8.03 ± o.55 | 8.06 | 8.07 | 7.87 | 8.30 ± 0.14 |
| WBC(×$10^9$/L) | 15.00 | 11.10 | 15.50 | 16.62 ± 0.14 | 17.10 | 15.60 | 13.30 | 15.33 ± 1.45 |
| Lymph(×$10^9$/L) | 10.30 | 4.30 | 9.30 | 12.56 ± 1.05 | 8.90 | 9.30 | 7.10 | 10.25 ± 2.24 |
| GRAN(×$10^9$/L) | 4.30 | 6.40 | 2.60 | 3.30 ± 0.86 | 3.60 | 5.90 | 5.80 | 2.93 ± 0.23 |
| PLT(×$10^9$/L) | 488.00 | 677.00 | 505.00 | 378.20 ± 4.85 | 521.00 | 471.00 | 453.00 | 428.00 ± 12.59 |

Control values were expressed as means ± SEM. The number in parentheses was number of mice used.

TABLE 6

Hematological Parameters of i.v. rhATF Treated Mice and Non-Treated Controls

| | Days after i.v. rhATF (n = 6) | | | | |
|---|---|---|---|---|---|
| | 10 | 20 | 30 | 40 | Controls(n = 9) |
| RBC(×10$^{12}$/L) | 8.43 ± 0.61 | 7.52 ± 1.15 | 6.77 ± 1.36 | 6.95 ± 1.60 | 8.15 ± 0.30 |
| WBC(×10$^9$/L) | 13.58 ± 4.26 | 13.12 ± 2.32 | 12.20 ± 2.34 | 11.63 ± 3.08 | 16.04 ± 0.70 |
| Lymph(×10$^9$/L) | 9.37 ± 4.21 | 6.83 ± 2.79 | 7.25 ± 1.83 | 7.07 ± 1.45 | 11.53 ± 1.23 |
| GRAN(×10$^9$/L) | 3.50 ± 1.60 | 4.70 ± 2.09 | 4.38 ± 1.32 | 3.95 ± 1.60 | 3.13 ± 0.47 |
| PLT(×10$^9$/L) | 409.33 ± 41.88 | 392.17 ± 77.20 | 359.50 ± 50.59 | 412.00 ± 96.35 | 400.30 ± 10.8 |

The mice were treated with rhATF (2.8 ug per mouse daily, i.v.) starting from the age of 12 weeks. Values were expressed as means ± SEM 4. Blood Lipid Analysis Levels of cholesterol, tri-glycerol, HDL and LDL of the treated animals were measured at the central laboratory in Nanjing University Hospital.

As shown in Table 7, no significant changes in blood lipid concentrations were observed in the rhATF treated rabbits. However, the levels of tri-glycerol and LDL-cholesterol were lower in the animals treated with intravenous injection of rhATF and rhATF vaccination, compared to control animals and animals treated with intravenous injection of rhATF alone. These data indicate that rhATF vaccination and intravenous administration had no significant effect on blood fibrinolysis, hematology and lipid levels in the treated animals.

TABLE 7

Blood Lipid Concentrations of Rabbits Treated with rhATF Vaccination or rhATF i.v.

| | TC | TG | HDL-C | LDL-C |
|---|---|---|---|---|
| Controls | 29.75 ± 4.63 | 0.85 ± 1.26 | 0.44 ± 0.16 | 13.58 ± 2.30 |
| rhATF i.v. | 22.05 ± 10.29 | 0.43 ± 0.40 | 0.42 ± 0.12 | 10.54 ± 4.00 |
| V + A | 12.9 ± 8.84** | 1.30 ± 0.84 | 0.34 ± 0.17* | 6.13 ± 4.12** |

TC indicates tri-glycerol; TG, total cholesterol; HDL-C, high density lipoprotein cholesterol; LDL-C, low density lipoprotein cholesterol; V + A, vaccination plus rhATF i.v.; Data is expressed as mmol/L, mean ± SD of 4 rabbits in one group.
*p < 0.05;
**p < 0.01.

Example 11

Determining MHC Class II Binding Epitopes in ATFs

MHC Class II binding sites of ATFs from human, yellow baboon, mouse, rat, cow, pig, and chicken were determined following the method described in Singh et al., Bioinformatics, 17(12):1236-37. The results are shown in Tables 8A-8G.

TABLE 8A

Human ATF

| Epitope | location of the first residue | number | proportion |
|---|---|---|---|
| YRGKASTDT (SEQ ID NO: 19) | 58 | 1 | 3% |
| WCYVQVGLK (SEQ ID NO: 20) | 112 | 2 | 6% |
| VGLKPLVQE (SEQ ID NO: 21) | 117 | 3 | 10% |

TABLE 8A-continued

Human ATF

| Epitope | location of the first residue | number | proportion |
|---|---|---|---|
| YVQVGLKPL (SEQ ID NO: 22) | 114 | 4 | 13% |
| MVHDCADGK (SEQ ID NO: 23) | 127 | 6 | 19% |

TABLE 8A-continued

Human ATF

| Epitope | location of the first residue | number | proportion |
|---|---|---|---|
| WNSATVLQQ (SEQ ID NO: 24) | 74 | 15 | 48% |
| total | | 31 | 100% |

TABLE 8B

Yellow Baboon ATF

| epitope | location of the first residue | number | proportion |
|---|---|---|---|
| YRGKASTDT (SEQ ID NO: 73) | 57 | 1 | 4% |
| WCYVQVGLK (SEQ ID NO: 74) | 111 | 2 | 8% |

TABLE 8B-continued

Yellow Baboon ATF

| epitope | location of the first residue | number | proportion |
|---|---|---|---|
| YVQVGLKQR (SEQ ID NO: 25) | 113 | 2 | 8% |
| VGLKQRVQE (SEQ ID NO: 26) | 116 | 4 | 17% |
| WNSATVLQQ (SEQ ID NO: 75) | 73 | 15 | 63% |
| total | | 24 | 100% |

TABLE 8C

Mouse ATF

| epitope | location of the first residue | number | proportion |
|---|---|---|---|
| YRGKANTDT (SEQ ID NO: 27) | 59 | 1 | 2% |
| FQCGQKALR (SEQ ID NO: 28) | 147 | 1 | 2% |
| FSRIRRCSC (SEQ ID NO: 29) | 26 | 2 | 3% |
| WCYVQIGLR (SEQ ID NO: 72) | 113 | 2 | 3% |
| IRRCSCPRK (SEQ ID NO: 31) | 29 | 3 | 5% |
| YVQIGLRQF (SEQ ID NO: 32) | 115 | 6 | 10% |
| VQIGLRQFV (SEQ ID NO: 33) | 116 | 6 | 10% |
| YKYFSRIRR (SEQ ID NO: 34) | 23 | 10 | 17% |
| MVHDCSLSK (SEQ ID NO: 35) | 128 | 11 | 19% |
| YFSRIRRCS (SEQ ID NO: 36) | 25 | 16 | 28% |
| total | | 58 | 100% |

TABLE 8D

Rat ATF

| epitope | location of the first residue | number | proportion |
|---|---|---|---|
| FSSIRRCSC (SEQ ID NO: 37) | 26 | 1 | 3% |
| YRGKANTDT (SEQ ID NO: 76) | 59 | 1 | 3% |
| FQCGQKALR (SEQ ID NO: 77) | 147 | 1 | 3% |
| WCYVQIGLK (SEQ ID NO: 38) | 113 | 2 | 6% |

TABLE 8D-continued

Rat ATF

| epitope | location of the first residue | number | proportion |
|---|---|---|---|
| IRRCSCPKK (SEQ ID NO: 39) | 29 | 3 | 8% |
| WNSPAVLQQ (SEQ ID NO: 40) | 75 | 3 | 8% |
| YFSSIRRCS (SEQ ID NO: 41) | 25 | 4 | 11% |
| YVQIGLKQF (SEQ ID NO: 42) | 115 | 4 | 11% |
| YKYFSSIRR (SEQ ID NO: 43) | 23 | 7 | 19% |
| MVQDCSLSK (SEQ ID NO: 44) | 128 | 10 | 28% |
| Total | | 36 | 100% |

TABLE 8E

Cow ATF

| Epitope | location of the first residue | number | proportion |
|---|---|---|---|
| FSNIQRCSC (SEQ ID NO: 45) | 27 | 1 | 1% |
| FQCGQKALR (SEQ ID NO: 78) | 148 | 1 | 1% |
| WCYVQIGLK (SEQ ID NO: 80) | 114 | 2 | 3% |
| YFSNIQRCS (SEQ ID NO: 46) | 26 | 4 | 6% |
| YVQIGLKQF (SEQ ID NO: 81) | 116 | 4 | 6% |
| YKYFSNIQR (SEQ ID NO: 47) | 24 | 6 | 9% |
| YRGKANRDL (SEQ ID NO: 48) | 59 | 7 | 10% |
| VQFCMVQDC (SEQ ID NO: 49) | 125 | 8 | 11% |
| VQIGLKQFV (SEQ ID NO: 50) | 117 | 8 | 11% |
| MVQDCSVGK (SEQ ID NO: 51) | 129 | 9 | 13% |
| LKMYHAHRS (SEQ ID NO: 52) | 83 | 20 | 29% |
| Total | | 70 | 100% |

TABLE 8F

Pig ATF

| epitope | location of the first residue | number | proportion |
|---|---|---|---|
| FSNIQRCSC (SEQ ID NO: 53) | 27 | 1 | 4% |
| YRGKANTNT (SEQ ID NO: 54) | 60 | 1 | 4% |
| FQCGQKALR (SEQ ID NO: 79) | 157 | 1 | 4% |
| WCYVQVGLK (SEQ ID NO: 55) | 114 | 2 | 8% |
| WNSATVLLN (SEQ ID NO: 56) | 76 | 3 | 12% |
| VGLKQLVQE (SEQ ID NO: 57) | 119 | 3 | 12% |
| YFSNIQRCS (SEQ ID NO: 58) | 26 | 4 | 16% |
| YVQVGLKQL (SEQ ID NO: 59) | 116 | 4 | 16% |
| YKYFSNIQR (SEQ ID NO: 60) | 24 | 6 | 24% |
| total | | 25 | 100% |

TABLE 8G

Chicken ATF

| epitope | location of the first residue | number | proportion |
|---|---|---|---|
| VYIRQYYKL (SEQ ID NO: 61) | 1 | 1 | 2% |
| VIRWGDYHA (SEQ ID NO: 62) | 84 | 1 | 2% |
| YYKLSHKHR (SEQ ID NO: 63) | 6 | 2 | 3% |
| YHADLKNAL (SEQ ID NO: 64) | 90 | 2 | 3% |
| WCYTKRRYS (SEQ ID NO: 65) | 118 | 2 | 3% |
| FFSQIKRCL (SEQ ID NO: 66) | 33 | 4 | 6% |
| LYWDHPSVI (SEQ ID NO: 67) | 77 | 6 | 10% |
| YRFFSQIKR (SEQ ID NO: 68) | 31 | 8 | 13% |
| YSIQETPCS (SEQ ID NO: 69) | 125 | 10 | 16% |
| IRQYYKLSH (SEQ ID NO: 70) | 3 | 26 | 42% |
| total | | 62 | 100% |

Example 12

Treating Atherosclerosis in a Human Patient

A human patient diagnosed with detectable atheromatous plaques is treated using a pharmaceutical composition containing an ATF and a carrier or an adjuvant prepared according to the methods described above. This composition contains rhATF in a pharmaceutically acceptable carrier and is administered intravenously to a patient at a dose of 100 mg (ATF) once a day. Additional administration is required if the titer of anti-ATF antibodies in the patient is lower than 1:10,000.

Other Embodiments

A number of embodiments of the invention have been described. Nevertheless, it will be understood that various modifications may be made without departing from the spirit and scope of the invention. Accordingly, other embodiments are within the scope of the following claims.

SEQUENCE LISTING

<160> NUMBER OF SEQ ID NOS: 81

<210> SEQ ID NO 1
<211> LENGTH: 157
<212> TYPE: PRT
<213> ORGANISM: Homo sapiens

<400> SEQUENCE: 1

Ser Asn Glu Leu His Gln Val Pro Ser Asn Cys Asp Cys Leu Asn Gly
 1               5                  10                  15

Gly Thr Cys Val Ser Asn Lys Tyr Phe Ser Asn Ile His Trp Cys Asn
             20                  25                  30

Cys Pro Lys Lys Phe Gly Gly Gln His Cys Glu Ile Asp Lys Ser Lys
         35                  40                  45

Thr Cys Tyr Glu Gly Asn Gly His Phe Tyr Arg Gly Lys Ala Ser Thr
50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125

His Asp Cys Ala Asp Gly Lys Lys Pro Ser Ser Pro Pro Glu Glu Leu
        130                 135                 140

Lys Phe Gln Cys Gly Gln Lys Thr Leu Arg Pro Arg Phe
145                 150                 155

<210> SEQ ID NO 2
<211> LENGTH: 155
<212> TYPE: PRT
<213> ORGANISM: Papio hamadryas

<400> SEQUENCE: 2

Ser Arg Glu Leu Gln Val Pro Ser Asp Cys Gly Cys Leu Asn Gly Gly
1               5                   10                  15

Thr Cys Met Ser Asn Lys Tyr Phe Ser Ser Ile His Trp Cys Asn Cys
                20                  25                  30

Pro Lys Lys Phe Gly Gly Gln His Cys Glu Ile Asp Lys Ser Lys Thr
            35                  40                  45

Cys Tyr Gly Asn Gly His Phe Tyr Arg Gly Lys Ala Ser Thr Asp Thr
        50                  55                  60

Met Gly Arg Ser Cys Leu Ala Trp Asn Ser Ala Thr Val Leu Gln Gln
65                  70                  75                  80

Thr Tyr His Ala His Arg Ser Asp Ala Leu Gln Leu Gly Leu Gly Lys
                85                  90                  95

His Asn Tyr Cys Arg Asn Pro Asp Asn Arg Arg Arg Pro Trp Cys Tyr
            100                 105                 110

Val Gln Val Gly Leu Lys Gln Arg Val Gln Glu Cys Met Val His Asn
            115                 120                 125

Cys Ala Asp Gly Lys Lys Pro Ser Ser Pro Pro Glu Glu Leu Gln Phe
        130                 135                 140

Gln Cys Gly Gln Arg Thr Leu Arg Pro Arg Phe
145                 150                 155

<210> SEQ ID NO 3
<211> LENGTH: 158
<212> TYPE: PRT
<213> ORGANISM: Mus musculus

<400> SEQUENCE: 3

Gly Ser Val Leu Gly Ala Pro Asp Glu Ser Asn Cys Gly Cys Gln Asn
1               5                   10                  15

Gly Gly Val Cys Val Ser Tyr Lys Tyr Phe Ser Arg Ile Arg Arg Cys
                20                  25                  30

Ser Cys Pro Arg Lys Phe Gln Gly Glu His Cys Glu Ile Asp Ala Ser
            35                  40                  45

Lys Thr Cys Tyr His Gly Asn Gly Asp Ser Tyr Arg Gly Lys Ala Asn
        50                  55                  60

```
Thr Asp Thr Lys Gly Arg Pro Cys Leu Ala Trp Asn Ala Pro Ala Val
65                  70                  75                  80

Leu Gln Lys Pro Tyr Asn Ala His Arg Pro Asp Ala Ile Ser Leu Gly
                85                  90                  95

Leu Gly Lys His Asn Tyr Cys Arg Asn Pro Asp Asn Lys Arg Pro
            100                 105                 110

Trp Cys Tyr Val Gln Ile Gly Leu Arg Gln Phe Val Gln Glu Cys Met
            115                 120                 125

Val His Asp Cys Ser Leu Ser Lys Pro Ser Ser Val Asp Gln
        130                 135                 140

Gln Gly Phe Gln Cys Gly Gln Lys Ala Leu Arg Pro Arg Phe
145                 150                 155

<210> SEQ ID NO 4
<211> LENGTH: 158
<212> TYPE: PRT
<213> ORGANISM: Rattus norvegicus

<400> SEQUENCE: 4

Gly Ser Glu Leu Glu Ala Ser Asp Glu Ser Asn Cys Gly Cys Gln Asn
1               5                   10                  15

Gly Gly Val Cys Val Ser Tyr Lys Tyr Phe Ser Ser Ile Arg Arg Cys
            20                  25                  30

Ser Cys Pro Lys Lys Phe Lys Gly Glu His Cys Glu Ile Asp Thr Ser
            35                  40                  45

Lys Thr Cys Tyr His Gly Asn Gly Gln Ser Tyr Arg Gly Lys Ala Asn
        50                  55                  60

Thr Asp Thr Lys Gly Arg Pro Cys Leu Ala Trp Asn Ser Pro Ala Val
65                  70                  75                  80

Leu Gln Gln Thr Tyr Asn Ala His Arg Ser Asp Ala Leu Ser Leu Gly
                85                  90                  95

Leu Gly Lys His Asn Tyr Cys Arg Asn Pro Asp Asn Arg Arg Pro
            100                 105                 110

Trp Cys Tyr Val Gln Ile Gly Leu Lys Gln Phe Val Gln Glu Cys Met
            115                 120                 125

Val Gln Asp Cys Ser Leu Ser Lys Lys Pro Ser Ser Thr Val Asp Gln
        130                 135                 140

Gln Gly Phe Gln Cys Gly Gln Lys Ala Leu Arg Pro Arg Phe
145                 150                 155

<210> SEQ ID NO 5
<211> LENGTH: 159
<212> TYPE: PRT
<213> ORGANISM: Bos taurus

<400> SEQUENCE: 5

Ser Asn Glu Val His Lys Glu Ser Gly Glu Ser Asn Cys Gly Cys Leu
1               5                   10                  15

Asn Gly Gly Lys Cys Val Thr Tyr Lys Tyr Phe Ser Asn Ile Gln Arg
            20                  25                  30

Cys Ser Cys Pro Lys Lys Phe Gln Gly Glu His Cys Glu Ile Asp Thr
            35                  40                  45

Ser Lys Thr Cys Tyr Gln Gly Asn Gly His Ser Tyr Arg Gly Lys Ala
        50                  55                  60

Asn Arg Asp Leu Ser Gly Arg Pro Cys Leu Ala Trp Asp Ser Pro Thr
65                  70                  75                  80

Val Leu Leu Lys Met Tyr His Ala His Arg Ser Asp Ala Ile Gln Leu
```

```
                        85                  90                  95
Gly Leu Gly Lys His Asn Tyr Cys Arg Asn Pro Asp Asn Gln Arg Arg
                100                 105                 110

Pro Trp Cys Tyr Val Gln Ile Gly Leu Lys Gln Phe Val Gln Phe Cys
            115                 120                 125

Met Val Gln Asp Cys Ser Val Gly Lys Ser Pro Ser Ser Pro Arg Glu
        130                 135                 140

Lys Glu Glu Phe Gln Cys Gly Lys Ala Leu Arg Pro Arg Phe
145                 150                 155

<210> SEQ ID NO 6
<211> LENGTH: 168
<212> TYPE: PRT
<213> ORGANISM: Sus scrofa

<400> SEQUENCE: 6

Ser His Glu Leu His Gln Glu Ser Gly Ala Ser Asn Cys Gly Cys Leu
1               5                   10                  15

Asn Gly Gly Lys Cys Val Ser Tyr Lys Tyr Phe Ser Asn Ile Gln Arg
                20                  25                  30

Cys Ser Cys Pro Lys Lys Phe Gln Gly Glu His Cys Glu Ile Asp Thr
            35                  40                  45

Ser Gln Thr Cys Phe Glu Gly Asn Gly His Ser Tyr Arg Gly Lys Ala
        50                  55                  60

Asn Thr Asn Thr Gly Gly Arg Pro Cys Leu Pro Trp Asn Ser Ala Thr
65                  70                  75                  80

Val Leu Leu Asn Thr Tyr His Ala His Arg Pro Asp Ala Leu Gln Leu
                85                  90                  95

Gly Leu Gly Lys His Asn Tyr Cys Arg Asn Pro Asp Asn Gln Arg Arg
                100                 105                 110

Pro Trp Cys Tyr Val Gln Val Gly Leu Lys Gln Leu Val Gln Glu Cys
            115                 120                 125

Met Val Pro Asn Cys Ser Gly Gly Glu Ser His Arg Pro Ala Tyr Asp
        130                 135                 140

Gly Lys Asn Pro Phe Ser Thr Pro Glu Lys Val Glu Phe Gln Cys Gly
145                 150                 155                 160

Gln Lys Ala Leu Arg Pro Arg Phe
                165

<210> SEQ ID NO 7
<211> LENGTH: 151
<212> TYPE: PRT
<213> ORGANISM: Gallus gallus

<400> SEQUENCE: 7

Val Tyr Ile Arg Gln Tyr Tyr Lys Leu Ser His Lys His Arg Pro Gln
1               5                   10                  15

His Arg Glu Cys Gln Cys Leu Asn Gly Gly Thr Cys Ile Thr Tyr Arg
                20                  25                  30

Phe Phe Ser Gln Ile Lys Arg Cys Leu Cys Pro Glu Gly Tyr Gly Gly
            35                  40                  45

Leu His Cys Glu Ile Asp Thr Asn Ser Ile Cys Tyr Ser Gly Asn Gly
        50                  55                  60

Glu Asp Tyr Arg Gly Met Ala Glu Asp Pro Gly Cys Leu Tyr Trp Asp
65                  70                  75                  80

His Pro Ser Val Ile Arg Trp Gly Asp Tyr His Ala Asp Leu Lys Asn
                85                  90                  95
```

Ala Leu Gln Leu Gly Leu Gly Lys His Asn Tyr Cys Arg Asn Pro Asn
            100                 105                 110

Gly Arg Ser Arg Pro Trp Cys Tyr Thr Lys Arg Arg Tyr Ser Ile Gln
            115                 120                 125

Glu Thr Pro Cys Ser Thr Ile Glu Lys Cys Glu Arg Thr Cys Gly Gln
130                 135                 140

Arg Ser Phe Ser Lys Tyr Phe
145                 150

<210> SEQ ID NO 8
<211> LENGTH: 322
<212> TYPE: PRT
<213> ORGANISM: Homo sapiens

<400> SEQUENCE: 8

Met Gly His Pro Pro Leu Leu Pro Leu Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Ala Val Thr Tyr Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
    130                 135                 140

Leu Asp Val Val Thr His Trp Ile Gln Glu Gly Glu Glu Gly Arg Pro
145                 150                 155                 160

Lys Asp Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly Arg Gln Cys Tyr Ser Cys Lys Gly Asn Ser Thr
    210                 215                 220

His Gly Cys Ser Ser Glu Glu Thr Phe Leu Ile Asp Cys Arg Gly Pro
225                 230                 235                 240

Met Asn Gln Cys Leu Val Ala Thr Asp Thr His Gly Pro Lys Asn Gln
                245                 250                 255

Ser Tyr Met Val Arg Gly Cys Ala Thr Ala Ser Met Cys Gln His Ala
            260                 265                 270

His Leu Gly Asp Ala Phe Ser Met Asn His Ile Asp Val Ser Cys Cys
        275                 280                 285

Thr Lys Ser Gly Cys Asn His Pro Asp Leu Asp Val Gln Tyr Arg Ser
    290                 295                 300

Gly Ala Ala Pro Gln Pro Gly Pro Ala His Leu Ser Leu Thr Ile Thr
305                 310                 315                 320

Leu Leu

<210> SEQ ID NO 9
<211> LENGTH: 120
<212> TYPE: PRT
<213> ORGANISM: Oryctolagus cuniculus

<400> SEQUENCE: 9

```
Cys Leu Asn Gly Gly Thr Cys Val Thr Tyr Lys Tyr Phe Ser Asn Ile
1               5                   10                  15

Trp Arg Cys Asn Cys Pro Lys Lys Phe Gln Gly Glu His Cys Glu Ile
            20                  25                  30

Asp Thr Leu Lys Thr Cys Tyr His Gly Asp Gly His Ser Tyr Arg Gly
        35                  40                  45

Lys Ala Asn Thr Asp Ile Met Asp Arg Pro Cys Leu Ala Trp Asn Ser
    50                  55                  60

Ala Asn Val Leu Thr Lys Thr Tyr His Ala His Arg Pro Asp Ala Leu
65                  70                  75                  80

Gln Leu Gly Leu Gly Lys His Asn Tyr Cys Arg Asn Pro Asp His Gln
                85                  90                  95

Arg Arg Pro Trp Cys Tyr Val Gln Val Gly Leu Lys Gln Leu Ile Gln
            100                 105                 110

Glu Cys Lys Val His Asp Cys Ser
        115                 120
```

<210> SEQ ID NO 10
<211> LENGTH: 120
<212> TYPE: PRT
<213> ORGANISM: Homo sapiens

<400> SEQUENCE: 10

```
Cys Leu Asn Gly Gly Thr Cys Val Ser Asn Lys Tyr Phe Ser Asn Ile
1               5                   10                  15

His Trp Cys Asn Cys Pro Lys Lys Phe Gly Gly Gln His Cys Glu Ile
            20                  25                  30

Asp Lys Ser Lys Thr Cys Tyr Glu Gly Asn Gly His Phe Tyr Arg Gly
        35                  40                  45

Lys Ala Ser Thr Asp Thr Met Gly Arg Pro Cys Leu Pro Trp Asn Ser
    50                  55                  60

Ala Thr Val Leu Gln Gln Thr Tyr His Ala His Arg Ser Asp Ala Leu
65                  70                  75                  80

Gln Leu Gly Leu Gly Lys His Asn Tyr Cys Arg Asn Pro Asp Asn Arg
                85                  90                  95

Arg Arg Pro Trp Cys Tyr Val Gln Val Gly Leu Lys Pro Leu Val Gln
            100                 105                 110

Glu Cys Met Val His Asp Cys Ala
        115                 120
```

<210> SEQ ID NO 11
<211> LENGTH: 120
<212> TYPE: PRT
<213> ORGANISM: Mus musculus

<400> SEQUENCE: 11

```
Cys Gln Asn Gly Gly Val Cys Val Ser Tyr Lys Tyr Phe Ser Arg Ile
1               5                   10                  15

Arg Arg Cys Ser Cys Pro Arg Lys Phe Gln Gly Glu His Cys Glu Ile
            20                  25                  30
```

```
Asp Ala Ser Lys Thr Cys Tyr His Gly Asn Gly Asp Ser Tyr Arg Gly
            35                  40                  45

Lys Ala Asn Thr Asp Thr Lys Gly Arg Pro Cys Leu Ala Trp Asn Ala
 50                  55                  60

Pro Ala Val Leu Gln Lys Pro Tyr Asn Ala His Arg Pro Asp Ala Ile
 65                  70                  75                  80

Ser Leu Gly Leu Gly Lys His Asn Tyr Cys Arg Asn Pro Asp Asn Gln
                 85                  90                  95

Lys Arg Pro Trp Cys Tyr Val Gln Ile Gly Leu Arg Gln Phe Val Gln
            100                 105                 110

Glu Cys Met Val His Asp Cys Ser
            115                 120

<210> SEQ ID NO 12
<211> LENGTH: 10
<212> TYPE: PRT
<213> ORGANISM: Homo sapiens

<400> SEQUENCE: 12

Val Ser Asn Lys Tyr Phe Ser Ile His Trp
 1               5                  10

<210> SEQ ID NO 13
<211> LENGTH: 11
<212> TYPE: PRT
<213> ORGANISM: Mus musculus

<400> SEQUENCE: 13

Val Ser Tyr Lys Tyr Phe Ser Arg Ile Arg Arg
 1               5                  10

<210> SEQ ID NO 14
<211> LENGTH: 11
<212> TYPE: PRT
<213> ORGANISM: Rattus norvegicus

<400> SEQUENCE: 14

Val Ser Tyr Lys Tyr Phe Ser Ser Ile Arg Arg
 1               5                  10

<210> SEQ ID NO 15
<211> LENGTH: 11
<212> TYPE: PRT
<213> ORGANISM: Bos taurus

<400> SEQUENCE: 15

Val Thr Tyr Lys Tyr Phe Ser Asn Ile Gln Arg
 1               5                  10

<210> SEQ ID NO 16
<211> LENGTH: 11
<212> TYPE: PRT
<213> ORGANISM: Sus scrofa

<400> SEQUENCE: 16

Val Ser Tyr Lys Tyr Phe Ser Asn Ile Gln Arg
 1               5                  10

<210> SEQ ID NO 17
<211> LENGTH: 11
<212> TYPE: PRT
<213> ORGANISM: Oryctolagus cuniculus
```

```
<400> SEQUENCE: 17

Val Thr Tyr Lys Tyr Phe Ser Asn Ile Trp Arg
 1               5                   10

<210> SEQ ID NO 18
<211> LENGTH: 11
<212> TYPE: PRT
<213> ORGANISM: Gallus gallus

<400> SEQUENCE: 18

Ile Thr Tyr Arg Phe Phe Ser Gln Ile Lys Arg
 1               5                   10

<210> SEQ ID NO 19
<211> LENGTH: 9
<212> TYPE: PRT
<213> ORGANISM: Homo sapiens

<400> SEQUENCE: 19

Tyr Arg Gly Lys Ala Ser Thr Asp Thr
 1               5

<210> SEQ ID NO 20
<211> LENGTH: 9
<212> TYPE: PRT
<213> ORGANISM: Homo sapiens

<400> SEQUENCE: 20

Trp Cys Tyr Val Gln Val Gly Leu Lys
 1               5

<210> SEQ ID NO 21
<211> LENGTH: 9
<212> TYPE: PRT
<213> ORGANISM: Homo sapiens

<400> SEQUENCE: 21

Val Gly Leu Lys Pro Leu Val Gln Glu
 1               5

<210> SEQ ID NO 22
<211> LENGTH: 9
<212> TYPE: PRT
<213> ORGANISM: Homo sapiens

<400> SEQUENCE: 22

Tyr Val Gln Val Gly Leu Lys Pro Leu
 1               5

<210> SEQ ID NO 23
<211> LENGTH: 9
<212> TYPE: PRT
<213> ORGANISM: Homo sapiens

<400> SEQUENCE: 23

Met Val His Asp Cys Ala Asp Gly Lys
 1               5

<210> SEQ ID NO 24
<211> LENGTH: 9
<212> TYPE: PRT
<213> ORGANISM: Homo sapiens

<400> SEQUENCE: 24

Trp Asn Ser Ala Thr Val Leu Gln Gln
```

<210> SEQ ID NO 25
<211> LENGTH: 9
<212> TYPE: PRT
<213> ORGANISM: Papio cynocephalus

<400> SEQUENCE: 25

Tyr Val Gln Val Gly Leu Lys Gln Arg
1               5

<210> SEQ ID NO 26
<211> LENGTH: 9
<212> TYPE: PRT
<213> ORGANISM: Papio cynocephalus

<400> SEQUENCE: 26

Val Gly Leu Lys Gln Arg Val Gln Glu
1               5

<210> SEQ ID NO 27
<211> LENGTH: 9
<212> TYPE: PRT
<213> ORGANISM: Mus musculus

<400> SEQUENCE: 27

Tyr Arg Gly Lys Ala Asn Thr Asp Thr
1               5

<210> SEQ ID NO 28
<211> LENGTH: 9
<212> TYPE: PRT
<213> ORGANISM: Mus musculus

<400> SEQUENCE: 28

Phe Gln Cys Gly Gln Lys Ala Leu Arg
1               5

<210> SEQ ID NO 29
<211> LENGTH: 9
<212> TYPE: PRT
<213> ORGANISM: Mus musculus

<400> SEQUENCE: 29

Phe Ser Arg Ile Arg Arg Cys Ser Cys
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Cys Tyr Val Gln Ile Gly Leu Arg Ile
1               5                   10

<210> SEQ ID NO 31
<211> LENGTH: 9
<212> TYPE: PRT
<213> ORGANISM: Mus musculus

<400> SEQUENCE: 31

Ile Arg Arg Cys Ser Cys Pro Arg Lys

```
<210> SEQ ID NO 32
<211> LENGTH: 9
<212> TYPE: PRT
<213> ORGANISM: Mus musculus

<400> SEQUENCE: 32

Tyr Val Gln Ile Gly Leu Arg Gln Phe
1               5

<210> SEQ ID NO 33
<211> LENGTH: 9
<212> TYPE: PRT
<213> ORGANISM: Mus musculus

<400> SEQUENCE: 33

Val Gln Ile Gly Leu Arg Gln Phe Val
1               5

<210> SEQ ID NO 34
<211> LENGTH: 9
<212> TYPE: PRT
<213> ORGANISM: Mus musculus

<400> SEQUENCE: 34

Tyr Lys Tyr Phe Ser Arg Ile Arg Arg
1               5

<210> SEQ ID NO 35
<211> LENGTH: 9
<212> TYPE: PRT
<213> ORGANISM: Mus musculus

<400> SEQUENCE: 35

Met Val His Asp Cys Ser Leu Ser Lys
1               5

<210> SEQ ID NO 36
<211> LENGTH: 9
<212> TYPE: PRT
<213> ORGANISM: Mus musculus

<400> SEQUENCE: 36

Tyr Phe Ser Arg Ile Arg Arg Cys Ser
1               5

<210> SEQ ID NO 37
<211> LENGTH: 9
<212> TYPE: PRT
<213> ORGANISM: Rattus norvegicus

<400> SEQUENCE: 37

Phe Ser Ser Ile Arg Arg Cys Ser Cys
1               5

<210> SEQ ID NO 38
<211> LENGTH: 9
<212> TYPE: PRT
<213> ORGANISM: Rattus norvegicus

<400> SEQUENCE: 38

Trp Cys Tyr Val Gln Ile Gly Leu Lys
1               5
```

```
<210> SEQ ID NO 39
<211> LENGTH: 9
<212> TYPE: PRT
<213> ORGANISM: Rattus norvegicus

<400> SEQUENCE: 39

Ile Arg Arg Cys Ser Cys Pro Lys Lys
1               5

<210> SEQ ID NO 40
<211> LENGTH: 9
<212> TYPE: PRT
<213> ORGANISM: Rattus norvegicus

<400> SEQUENCE: 40

Trp Asn Ser Pro Ala Val Leu Gln Gln
1               5

<210> SEQ ID NO 41
<211> LENGTH: 9
<212> TYPE: PRT
<213> ORGANISM: Rattus norvegicus

<400> SEQUENCE: 41

Tyr Phe Ser Ser Ile Arg Arg Cys Ser
1               5

<210> SEQ ID NO 42
<211> LENGTH: 9
<212> TYPE: PRT
<213> ORGANISM: Rattus norvegicus

<400> SEQUENCE: 42

Tyr Val Gln Ile Gly Leu Lys Gln Phe
1               5

<210> SEQ ID NO 43
<211> LENGTH: 9
<212> TYPE: PRT
<213> ORGANISM: Rattus norvegicus

<400> SEQUENCE: 43

Tyr Lys Tyr Phe Ser Ser Ile Arg Arg
1               5

<210> SEQ ID NO 44
<211> LENGTH: 9
<212> TYPE: PRT
<213> ORGANISM: Rattus norvegicus

<400> SEQUENCE: 44

Met Val Gln Asp Cys Ser Leu Ser Lys
1               5

<210> SEQ ID NO 45
<211> LENGTH: 9
<212> TYPE: PRT
<213> ORGANISM: Bos taurus

<400> SEQUENCE: 45

Phe Ser Asn Ile Gln Arg Cys Ser Cys
1               5

<210> SEQ ID NO 46
<211> LENGTH: 9
<212> TYPE: PRT
```

<213> ORGANISM: Bos taurus

<400> SEQUENCE: 46

Tyr Phe Ser Asn Ile Gln Arg Cys Ser
1               5

<210> SEQ ID NO 47
<211> LENGTH: 9
<212> TYPE: PRT
<213> ORGANISM: Bos taurus

<400> SEQUENCE: 47

Tyr Lys Tyr Phe Ser Asn Ile Gln Arg
1               5

<210> SEQ ID NO 48
<211> LENGTH: 9
<212> TYPE: PRT
<213> ORGANISM: Bos taurus

<400> SEQUENCE: 48

Tyr Arg Gly Lys Ala Asn Arg Asp Leu
1               5

<210> SEQ ID NO 49
<211> LENGTH: 9
<212> TYPE: PRT
<213> ORGANISM: Bos taurus

<400> SEQUENCE: 49

Val Gln Phe Cys Met Val Gln Asp Cys
1               5

<210> SEQ ID NO 50
<211> LENGTH: 9
<212> TYPE: PRT
<213> ORGANISM: Bos taurus

<400> SEQUENCE: 50

Val Gln Ile Gly Leu Lys Gln Phe Val
1               5

<210> SEQ ID NO 51
<211> LENGTH: 9
<212> TYPE: PRT
<213> ORGANISM: Bos taurus

<400> SEQUENCE: 51

Met Val Gln Asp Cys Ser Val Gly Lys
1               5

<210> SEQ ID NO 52
<211> LENGTH: 9
<212> TYPE: PRT
<213> ORGANISM: Bos taurus

<400> SEQUENCE: 52

Leu Lys Met Tyr His Ala His Arg Ser
1               5

<210> SEQ ID NO 53
<211> LENGTH: 9
<212> TYPE: PRT
<213> ORGANISM: Sus scrofa

<400> SEQUENCE: 53

```
Phe Ser Asn Ile Gln Arg Cys Ser Cys
1               5
```

<210> SEQ ID NO 54
<211> LENGTH: 9
<212> TYPE: PRT
<213> ORGANISM: Sus scrofa

<400> SEQUENCE: 54

```
Tyr Arg Gly Lys Ala Asn Thr Asn Thr
1               5
```

<210> SEQ ID NO 55
<211> LENGTH: 9
<212> TYPE: PRT
<213> ORGANISM: Sus scrofa

<400> SEQUENCE: 55

```
Trp Cys Tyr Val Gln Val Gly Leu Lys
1               5
```

<210> SEQ ID NO 56
<211> LENGTH: 9
<212> TYPE: PRT
<213> ORGANISM: Sus scrofa

<400> SEQUENCE: 56

```
Trp Asn Ser Ala Thr Val Leu Leu Asn
1               5
```

<210> SEQ ID NO 57
<211> LENGTH: 9
<212> TYPE: PRT
<213> ORGANISM: Sus scrofa

<400> SEQUENCE: 57

```
Val Gly Leu Lys Gln Leu Val Gln Glu
1               5
```

<210> SEQ ID NO 58
<211> LENGTH: 9
<212> TYPE: PRT
<213> ORGANISM: Sus scrofa

<400> SEQUENCE: 58

```
Tyr Phe Ser Asn Ile Gln Arg Cys Ser
1               5
```

<210> SEQ ID NO 59
<211> LENGTH: 9
<212> TYPE: PRT
<213> ORGANISM: Sus scrofa

<400> SEQUENCE: 59

```
Tyr Val Gln Val Gly Leu Lys Gln Leu
1               5
```

<210> SEQ ID NO 60
<211> LENGTH: 9
<212> TYPE: PRT
<213> ORGANISM: Sus scrofa

<400> SEQUENCE: 60

```
Tyr Lys Tyr Phe Ser Asn Ile Gln Arg
1               5
```

```
<210> SEQ ID NO 61
<211> LENGTH: 9
<212> TYPE: PRT
<213> ORGANISM: Gallus gallus

<400> SEQUENCE: 61

Val Tyr Ile Arg Gln Tyr Tyr Lys Leu
1               5

<210> SEQ ID NO 62
<211> LENGTH: 9
<212> TYPE: PRT
<213> ORGANISM: Gallus gallus

<400> SEQUENCE: 62

Val Ile Arg Trp Gly Asp Tyr His Ala
1               5

<210> SEQ ID NO 63
<211> LENGTH: 9
<212> TYPE: PRT
<213> ORGANISM: Gallus gallus

<400> SEQUENCE: 63

Tyr Tyr Lys Leu Ser His Lys His Arg
1               5

<210> SEQ ID NO 64
<211> LENGTH: 9
<212> TYPE: PRT
<213> ORGANISM: Gallus gallus

<400> SEQUENCE: 64

Tyr His Ala Asp Leu Lys Asn Ala Leu
1               5

<210> SEQ ID NO 65
<211> LENGTH: 9
<212> TYPE: PRT
<213> ORGANISM: Gallus gallus

<400> SEQUENCE: 65

Trp Cys Tyr Thr Lys Arg Arg Tyr Ser
1               5

<210> SEQ ID NO 66
<211> LENGTH: 9
<212> TYPE: PRT
<213> ORGANISM: Gallus gallus

<400> SEQUENCE: 66

Phe Phe Ser Gln Ile Lys Arg Cys Leu
1               5

<210> SEQ ID NO 67
<211> LENGTH: 9
<212> TYPE: PRT
<213> ORGANISM: Gallus gallus

<400> SEQUENCE: 67

Leu Tyr Trp Asp His Pro Ser Val Ile
1               5

<210> SEQ ID NO 68
```

```
<211> LENGTH: 9
<212> TYPE: PRT
<213> ORGANISM: Gallus gallus

<400> SEQUENCE: 68

Tyr Arg Phe Phe Ser Gln Ile Lys Arg
1               5

<210> SEQ ID NO 69
<211> LENGTH: 9
<212> TYPE: PRT
<213> ORGANISM: Gallus gallus

<400> SEQUENCE: 69

Tyr Ser Ile Gln Glu Thr Pro Cys Ser
1               5

<210> SEQ ID NO 70
<211> LENGTH: 9
<212> TYPE: PRT
<213> ORGANISM: Gallus gallus

<400> SEQUENCE: 70

Ile Arg Gln Tyr Tyr Lys Leu Ser His
1               5

<210> SEQ ID NO 71
<211> LENGTH: 9
<212> TYPE: PRT
<213> ORGANISM: Oryctolagus cuniculus

<400> SEQUENCE: 71

Tyr Lys Tyr Phe Ser Asn Ile Trp Arg
1               5

<210> SEQ ID NO 72
<211> LENGTH: 9
<212> TYPE: PRT
<213> ORGANISM: Mus musculus

<400> SEQUENCE: 72

Trp Cys Tyr Val Gln Ile Gly Leu Arg
1               5

<210> SEQ ID NO 73
<211> LENGTH: 9
<212> TYPE: PRT
<213> ORGANISM: Papio cynocephalus

<400> SEQUENCE: 73

Tyr Arg Gly Lys Ala Ser Thr Asp Thr
1               5

<210> SEQ ID NO 74
<211> LENGTH: 9
<212> TYPE: PRT
<213> ORGANISM: Papio cynocephalus

<400> SEQUENCE: 74

Trp Cys Tyr Val Gln Val Gly Leu Lys
1               5

<210> SEQ ID NO 75
<211> LENGTH: 9
<212> TYPE: PRT
<213> ORGANISM: Papio cynocephalus
```

```
<400> SEQUENCE: 75

Trp Asn Ser Ala Thr Val Leu Gln Gln
1               5

<210> SEQ ID NO 76
<211> LENGTH: 9
<212> TYPE: PRT
<213> ORGANISM: Rattus norvegicus

<400> SEQUENCE: 76

Tyr Arg Gly Lys Ala Asn Thr Asp Thr
1               5

<210> SEQ ID NO 77
<211> LENGTH: 9
<212> TYPE: PRT
<213> ORGANISM: Rattus norvegicus

<400> SEQUENCE: 77

Phe Gln Cys Gly Gln Lys Ala Leu Arg
1               5

<210> SEQ ID NO 78
<211> LENGTH: 9
<212> TYPE: PRT
<213> ORGANISM: Bos taurus

<400> SEQUENCE: 78

Phe Gln Cys Gly Gln Lys Ala Leu Arg
1               5

<210> SEQ ID NO 79
<211> LENGTH: 9
<212> TYPE: PRT
<213> ORGANISM: Sus scrofa

<400> SEQUENCE: 79

Phe Gln Cys Gly Gln Lys Ala Leu Arg
1               5

<210> SEQ ID NO 80
<211> LENGTH: 9
<212> TYPE: PRT
<213> ORGANISM: Bos taurus

<400> SEQUENCE: 80

Trp Cys Tyr Val Gln Ile Gly Leu Lys
1               5

<210> SEQ ID NO 81
<211> LENGTH: 9
<212> TYPE: PRT
<213> ORGANISM: Bos taurus

<400> SEQUENCE: 81

Tyr Val Gln Ile Gly Leu Lys Gln Phe
1               5
```

What is claimed is:

1. A method of treating atherosclerosis, the method comprising administering to a patient suffering from or at risk for atherosclerosis a therapeutically effective amount of a pharmaceutical composition comprising an amino terminal fragment (ATF) polypeptide, wherein the ATF polypeptide consists of 157 amino acids or less with an amino acid sequence that is at least 90% identical to SEQ ID NO:1 and is capable of either binding to a urokinase plasminogen activator receptor (uPAR) or inducing an anti-ATF immune response in the patient, thereby treating atherosclerosis.

2. The method of claim 1, wherein the composition is administered to the patient before atherosclerosis development in the patient.

3. The method of claim 1, wherein the composition is administered to the patient after atherosclerosis development in the patient.

4. The method of claim 1, wherein the ATF polypeptide consists of an amino acid sequence that is at least 95% identical to SEQ ID NO:1.

5. The method of claim 1, wherein the ATF polypeptide consists of an amino acid sequence that is at least 99% identical to SEQ ID NO:1.

6. The method of claim 1, wherein the ATF polypeptide consists of the amino acid sequence of SEQ ID NO:1.

7. The method of claim 1, wherein the composition comprises an adjuvant.

8. The method of claim 1, wherein the ATF polypeptide is conjugated with polyethylene glycol.

9. The method of claim 1, wherein the ATF polypeptide is fused to albumin.

10. The method of claim 1, wherein the composition is administered intravenously.

11. The method of claim 1, wherein the composition is administered to the patient before and after atherosclerosis development in the patient

* * * * *

UNITED STATES PATENT AND TRADEMARK OFFICE
CERTIFICATE OF CORRECTION

PATENT NO. : 8,507,646 B2
APPLICATION NO. : 12/528300
DATED : August 13, 2013
INVENTOR(S) : Jian-ning Liu Page 1 of 1

It is certified that error appears in the above-identified patent and that said Letters Patent is hereby corrected as shown below:

On the Title page, after Inventor, delete "Jian-Ning Liu" and insert -- Jian-ning Liu --.

On the Title page, right column, line 16, under Other Publications, delete "Mactrophage" and insert -- Macrophage --.

In the Claims:

In Column 58, line 18, Claim 11, delete "patient" and insert -- patient. --.

Signed and Sealed this
Fifth Day of November, 2013

Teresa Stanek Rea
*Deputy Director of the United States Patent and Trademark Office*